US012339205B2

(12) United States Patent
Kawasaki et al.

(10) Patent No.: US 12,339,205 B2
(45) Date of Patent: Jun. 24, 2025

(54) METHOD FOR RECOVERING EXTRACELLULAR VESICLES

(71) Applicant: H.U. Group Research Institute G.K., Hachioji (JP)

(72) Inventors: Yuki Kawasaki, Tokyo (JP); Ayako Kurimoto, Tokyo (JP); Tatsutoshi Inuzuka, Tokyo (JP)

(73) Assignee: H.U. Group Research Institute G. K., Hachioji (JP)

( * ) Notice: Subject to any disclaimer, the term of this patent is extended or adjusted under 35 U.S.C. 154(b) by 1077 days.

(21) Appl. No.: 17/284,963

(22) PCT Filed: Oct. 16, 2019

(86) PCT No.: PCT/JP2019/040612
§ 371 (c)(1),
(2) Date: Apr. 13, 2021

(87) PCT Pub. No.: WO2020/080387
PCT Pub. Date: Apr. 23, 2020

(65) Prior Publication Data
US 2021/0396633 A1   Dec. 23, 2021

(30) Foreign Application Priority Data

Oct. 17, 2018 (JP) ................................ 2018-195926
Jan. 31, 2019 (JP) ................................ 2019-015177

(51) Int. Cl.
| | | |
|---|---|---|
| G01N 1/04 | (2006.01) | |
| C12Q 1/6886 | (2018.01) | |
| G01N 1/40 | (2006.01) | |
| G01N 33/48 | (2006.01) | |
| G01N 33/50 | (2006.01) | |
| G01N 33/567 | (2006.01) | |

(52) U.S. Cl.
CPC ......... *G01N 1/4077* (2013.01); *C12Q 1/6886* (2013.01); *G01N 33/5076* (2013.01); *G01N 33/567* (2013.01)

(58) Field of Classification Search
None
See application file for complete search history.

(56) References Cited

U.S. PATENT DOCUMENTS

| | | |
|---|---|---|
| 2009/0258379 A1 | 10/2009 | Klein et al. |
| 2013/0273544 A1 | 10/2013 | Vlassov et al. |
| 2015/0125864 A1 | 5/2015 | Kang et al. |
| 2015/0184248 A1 | 7/2015 | Tsuchiya et al. |
| 2016/0024503 A1 | 1/2016 | Kalluri et al. |
| 2016/0349246 A1 | 12/2016 | Fujii et al. |
| 2018/0028687 A1 | 2/2018 | Selaru et al. |
| 2018/0120299 A1 | 5/2018 | Nishibu et al. |
| 2018/0164197 A1 | 6/2018 | Park et al. |
| 2020/0041391 A1 | 2/2020 | Inuzuka et al. |
| 2020/0255831 A1 | 8/2020 | Kalluri et al. |

FOREIGN PATENT DOCUMENTS

| | | |
|---|---|---|
| CN | 105723221 A | 6/2016 |
| CN | 107002072 A | 8/2017 |
| CN | 107532195 A | 1/2018 |
| CN | 108546671 A | 9/2018 |
| JP | 2007-271388 A | 10/2007 |
| JP | 2017-38566 A | 2/2017 |
| JP | 2017-120263 A | 7/2017 |
| KR | 10-2015-0145720 A | 12/2015 |
| KR | 2016-0116802 A | 10/2016 |
| KR | 10-1895916 B1 | 9/2018 |
| WO | WO 2014/003053 A1 | 1/2014 |
| WO | WO 2014/152622 A1 | 9/2014 |
| WO | WO 2017/123933 A1 | 7/2017 |
| WO | WO 2017/178472 A1 | 10/2017 |
| WO | WO 2018/070479 A1 | 4/2018 |

OTHER PUBLICATIONS

Combined Chinese Office Action and Search Report issued on Sep. 27, 2023 in Chinese Patent Application No. 201980068028 (with unedited computer-generated English translation of Office Action only), 15 pages.
Extended European Search Report issued Jul. 8, 2022 in European Patent Application No. 19874334.6, 7 pages.
European Office Action issued May 26, 2023 in European Patent Application No. 19874334.6, 5 pages.
International Search Report issued on PCT/JP2019/040612 filed on Oct. 16, 2019, 2 pages.
Japanese Office Action issued Dec. 5, 2023 in Japanese Patent Application No. 2020-553220 (with unedited computer-generated English translation), 8 pages.
Chinese Office Action Apr. 16, 2024 in corresponding Chinese Patent Application No. 201980068028.X (with English translation), 16 pages.

*Primary Examiner* — Jennifer E Graser
(74) *Attorney, Agent, or Firm* — Oblon, McClelland, Maier & Neustadt, L.L.P.

(57) ABSTRACT

A method involves recovery an extracellular vesicle from an extracellular vesicle-containing sample. Such a method of recovering the extracellular vesicle may include separating the extracellular vesicle from the extracellular vesicle-containing sample in the presence of a polymer.

19 Claims, 15 Drawing Sheets

Specification includes a Sequence Listing.

```
SEQUENCE LISTING

<160> NUMBER OF SEQ ID NOS: 3

<210> SEQ ID NO 1
<211> LENGTH: 26
<212> TYPE: DNA
<213> ORGANISM: Artificial Sequence
<220> FEATURE:
<223> OTHER INFORMATION: Forward primer for detecting EML4-ALK mRNA

<400> SEQUENCE: 1
cagatgatag ccgtaataaa ttgtcg                                        26

<210> SEQ ID NO 2
<211> LENGTH: 19
<212> TYPE: DNA
<213> ORGANISM: Artificial Sequence
<220> FEATURE:
<223> OTHER INFORMATION: Reverse primer for detecting EML4-ALK mRNA

<400> SEQUENCE: 2
cttccggcgg tacacttgg                                                19

<210> SEQ ID NO 3
<211> LENGTH: 25
<212> TYPE: DNA
<213> ORGANISM: Artificial Sequence
<220> FEATURE:
<223> OTHER INFORMATION: Fluorescent probe for detecting EML4-ALK mRNA

<400> SEQUENCE: 3
actgcagaca agcataaaga tgtca                                         25
```

METHOD FOR RECOVERING EXTRACELLULAR VESICLES

SEQUENCE LISTING

The instant application contains a Sequence Listing which has been submitted electronically in ASCII format and is hereby incorporated by reference in its entirety. Said ASCII copy, created on Aug. 10, 2021, is named 536396USSL.txt and is 1029 bytes in size.

TECHNICAL FIELD

The present invention relates to a method of recovering extracellular vesicle(s), and the like.

BACKGROUND ART

An extracellular vesicle (EV) is a microscopic vesicle secreted from various types of cells and having a membrane structure, and exists in body fluids such as blood or cell culturing medium. The extracellular vesicles secreted extracellularly include exosomes, ectosomes, and apoptotic blebs. Since the extracellular vesicle refers to various groups that contain various substances that play a function such as intercellular signaling, it has been analyzed for the purposes of diagnosis, drug discovery and the like. Thus, it is required to develop a method of recovering the extracellular vesicles useful for such analyses. For example, Patent Literature 1 describes a method of recovering extracellular vesicles with use of a chelating agent.

PRIOR ART REFERENCES

Patent Literature

Patent Literature 1: International Patent Application Publication No. 2018/070479

SUMMARY OF INVENTION

Problem to be Solved by the Invention

If extracellular vesicles can be recovered from an extracellular vesicle-containing sample at a high efficiency, such extracellular vesicles are promising for application to diagnosis, drug discovery and the like. The extracellular vesicle(s) can be recovered mainly by an immunoprecipitation method using an antibody against an extracellular vesicle marker or an ultracentrifugal method. However, in such a method, the extracellular vesicle cannot be always recovered at a high efficiency. As well, such a method causes unevenness in product quality because the recovered extracellular vesicle was concentrated unspecifically.

Therefore, it is an object of the present invention to develop a new method for recovering extracellular vesicle(s).

Solution to Problem

As a result of an extensive study, the present inventors have found that extracellular vesicle(s) can be recovered at a high efficiency by separating the extracellular vesicle(s) from the extracellular vesicle-containing sample in the presence of a predetermined polymer and so on, and completed the present invention.

That is, the present inventions are as follows.

[1] A method of recovering an extracellular vesicle, the method comprising separating the extracellular vesicle from an extracellular vesicle-containing sample in the presence of a polymer.

[2] The method according to [1], wherein the polymer has a value of 1.5 mPa·s or more as a viscosity in 1 to 20 wt % aqueous solution at 20 to 30° C.

[3] The method according to [1] or [2], wherein the polymer is a cellulose derivative, or a polyvinyl derivative having a carbonyl-containing hydrophilic group.

[4] The method according to [3], wherein the polymer is a cellulose derivative in which a hydrogen atom in at least one hydroxy group is substituted with a carboxyalkyl or hydroxyalkyl, or a polyvinyl derivative in which at least one hydrogen atom is substituted with a lactam.

[5] The method according to [4], wherein the polymer is carboxymethyl cellulose, hydroxyethyl cellulose, hydroxypropyl cellulose, hydroxypropylmethyl cellulose or polyvinylpyrrolidone.

[6] The method according to any of [1] to [5], wherein the polymer has a weight average molecular weight of 10 kDa or more.

[7] The method according to any of [1] to [6], wherein a concentration of the polymer used in the separation of the extracellular vesicle from the extracellular vesicle-containing sample ranges from 0.01 to 10.00 wt %.

[8] The method according to any of [1] to [7], further comprising mixing the extracellular vesicle-containing sample with a chelating agent.

[9] The method according to any of [1] to [8], wherein the extracellular vesicle is exosome.

[10] The method according to any of [1] to [9], wherein the separation is performed by a separation using an extracellular vesicle membrane-binding material or an ultracentrifugal method of the extracellular vesicle-containing sample.

[11] The method according to [10], wherein the extracellular vesicle membrane-binding material is an antibody against a tetraspanin membrane protein or an antibody against an extracellular matrix metalloproteinase inducer.

[12] The method according to [11], wherein the extracellular vesicle membrane-binding material is an antibody against CD9, CD63, CD81 or CD147.

[13] The method according to any of [1] to [12], wherein the extracellular vesicle-containing sample is a blood sample, urine or saliva.

[14] A method of analyzing an extracellular vesicle, the method comprising:
(1) separating the extracellular vesicle from an extracellular vesicle-containing sample in the presence of a polymer; and
(2) analyzing the separated extracellular vesicle.

[15] The method according to [14], further comprising adding a chelating agent to the extracellular vesicle-containing sample.

[16] The method according to [14] or [15], further comprising analyzing a protein or a nucleic acid in the separated extracellular vesicle.

[17] A kit comprising a polymer and an extracellular vesicle membrane-binding material.

[18] The kit according to [17], further comprising a chelating agent.

Effect of the Invention

According to the present invention, it is possible to recover the extracellular vesicle(s) at a high efficiency and a high purity with use of a predetermined polymer.

EMBODIMENTS FOR CARRYING OUT THE INVENTION

Figure 1:
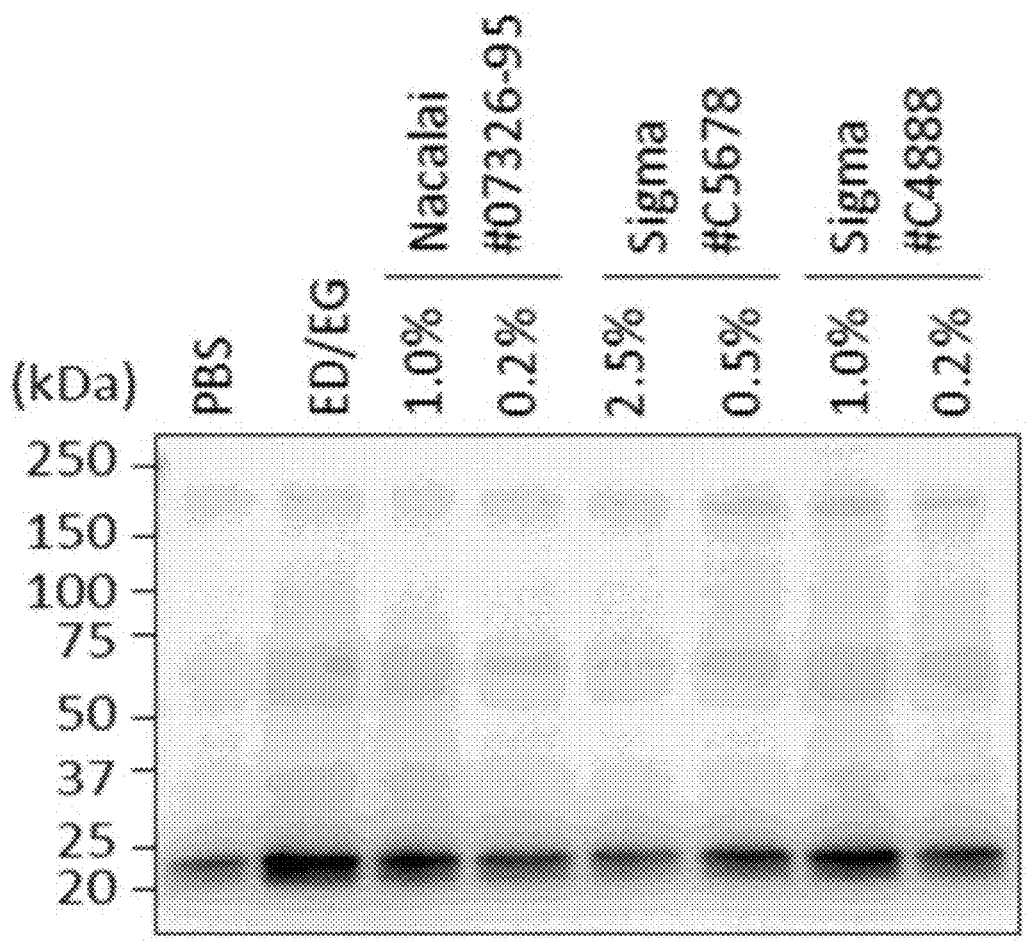
FIG. 1 is a diagram depicting results of a western blotting with a biotinylated anti-CD9 antibody of samples obtained from an immunoprecipitation method using an anti-CD9 antibody for a serum specimen that is diluted with PBS, EDTA/EGTA-PBS ("ED/EG") or each of various CMC-PBS at different concentrations in Example 1.

The present invention provides a method of recovering an extracellular vesicle.

The extracellular vesicle is a microscopic vesicle secreted from various types of cells and having a membrane structure. Examples of the extracellular vesicle include exosomes, ectosomes and apoptotic blebs. Preferably, the extracellular vesicle is the exosome. The extracellular vesicle can also be defined by its size. The size of the extracellular vesicle is, for example, 30 to 1000 nm, preferably 50 to 300 nm, and more preferably 80 to 200 nm. The size of the extracellular vesicle can be measured by, for example, a method based on Brownian movement of the extracellular vesicle, a light scattering method, and an electric resistance method, and the like. Preferably, the size of the extracellular vesicle is measured by NanoSight (manufactured by Malvern Instruments).

The method of recovering of the present invention includes the following step:
(1) separating the extracellular vesicle(s) from the extracellular vesicle-containing sample in the presence of a polymer.

The extracellular vesicle-containing sample is any sample that contains the extracellular vesicle. Preferably, the extracellular vesicle-containing sample is a biological liquid sample. The extracellular vesicle-containing sample may be subjected to another treatment before being used for the method of the present invention. Examples of such a treatment include centrifugation, extraction, filtration, precipitation, heating, freezing, refrigeration, and stirring.

In one embodiment, the extracellular vesicle-containing sample is a culture supernatant. The culture supernatant may be a cell culture supernatant or a tissue culture supernatant. Examples of the organism from which a cell or a tissue to be cultured is derived include animals such as mammalian animals (e.g., primates such as humans and monkeys; rodents such as mice, rats and rabbits; farm animals such as cattle, pigs and goats; and working animals such as horses and sheep) and birds (e.g., chickens), insects, microorganisms (e.g., bacteria), plants and fish. Preferably, the organisms are mammalian animals such as humans.

In another embodiment, the extracellular vesicle-containing sample is a body fluid. The body fluid is derived from the organism as described above. Examples of the body fluid include blood samples (e.g., whole blood, serum and plasma), urine, saliva, lymph fluid, tissue fluid, cerebrospinal fluid, ascites, sweat, seminal fluid, tear fluid, mucosal fluid, milk, thoracic fluid, bronchoalveolar lavage fluid and amnion fluid. Preferably, the body fluid is blood sample, urine or saliva. Examples of the plasma include heparin plasma, citrate plasma, sodium fluoride plasma, and a plasma that contains acid-citrate-dextrose (ACD) or citrate phosphate dextrose (CPD). In general, compared to culture supernatant, it is difficult to recover extracellular vesicles in a body fluid (e.g., blood, urine and saliva) that contains more proteins (e.g., albumin, lysozyme, lactoferrin, histatin, peroxidase, agglutinin, defensin and immunoglobulin) than the culture supernatant. Meanwhile, according to the present invention, it is possible to increase an amount of recovering the extracellular vesicles from the extracellular vesicle-containing sample, and recover the extracellular vesicles at a high efficiency and high purity even from such a body fluid.

The polymer used in the present invention is preferably a water-soluble polymer. The "water-soluble polymer" refers to a polymer with a solubility of 0.01 wt % or more in water at 4 to 80° C. (preferably 4 to 37° C.). The solubility of water-soluble polymer in water at 4 to 80° C. (preferably 4 to 37° C.) may be preferably 0.05 wt % or more, more preferably 0.1 wt % or more.

In order to accomplish the object of the present invention, the polymer may have a value of 1.5 mPa·s or more as a viscosity in an aqueous solution with 1 to 20 wt % at 20 to 30° C., for example. The viscosity of the polymer under the above condition may be preferably 5 mPa·s or more, more preferably 10 mPa·s or more, still more preferably 20 mPa·s or more, still further more preferably 30 mPa·s or more, and particularly preferably 35 mPa·s or more. The viscosity of the polymer under the above condition may be preferably 30000 mPa·s or less, more preferably 20000 mPa·s or less, still more preferably 10000 mPa·s or less, still further more preferably 5000 mPa·s or less, and particularly preferably 1000 mPa·s or less. More specifically, the viscosity of the polymer under the above condition may be preferably 5 to 30000 mPa·s, more preferably 10 to 20000 mPa·s, still more preferably 20 to 10000 mPa·s, still further more preferably 30 to 5000 mPa·s, and particularly preferably 35 to 1000 mPa·s.

In order to accomplish the object of the present invention, the polymer may have a value of 1.5 mPa·s or more as a viscosity at 30° C. in a phosphate-buffered saline (PBS) solution that is prepared by dissolving the polymer in the PBS to achieve 2 wt %, for example. The viscosity of the polymer under the above condition may be preferably 5 mPa·s or more, more preferably 10 mPa·s or more, still more preferably 20 mPa·s or more, still further more preferably 30 mPa·s or more, and particularly preferably 35 mPa·s or more. The viscosity of the polymer under the above condition may be preferably 30000 mPa·s or less, more preferably 20000 mPa·s or less, still more preferably 10000 mPa·s or less, still further more preferably 5000 mPa·s or less, and particularly preferably 1000 mPa·s or less. More specifically, the viscosity of the polymer under the above condition may be preferably 5 to 30000 mPa·s, more preferably 10 to 20000 mPa·s, still more preferably 20 to 10000 mPa·s, still further more preferably 30 to 5000 mPa·s, and particularly preferably 35 to 1000 mPa·s.

The viscosity of the polymer can be measured by either a method (method of using a rotary viscometer) of detecting a viscosity friction torque of liquid generated at an exterior periphery of a rotor while a liquid sample is rotated by the rotor, or a method (method of using falling ball viscometer) of measuring a falling time while a falling weight falls freely inside a measurement tube filled with the sample. The viscosity of the polymer can be measured by a method (method of using vibration viscometer) of measuring an amount of input electric current while an oscillator driving current is increased so as to maintain a constant vibration amplitude by overcoming a force that refers to a vibration amplitude of a sensor, for example. The vibration amplitude of the sensor is decreased with an increase in a liquid viscosity due to its viscosity resistance when an oscillator (viscosity sensor) is put inside the liquid sample and vibrated.

The viscosity of the polymer can be measured with a viscosity analyzer (e.g., Rheology Spectrometer SKR100 manufactured by Yamato Scientific Co., Ltd.), for example.

The polymer may be a cellulose derivative, a polyvinyl derivative having a hydrophilic group, or a polyether compound, for example.

The cellulose derivative is a cellulose derivative in which a hydrogen atom in at least one hydroxy group of the cellulose is substituted with a hydrophilic group. Examples of the hydrophilic group in the cellulose derivative include carboxyalkyl (e.g., carboxy $C_{1-6}$ alkyl) and hydroxyalkyl (e.g., hydroxy $C_{1-6}$ alkyl). The hydrophilic group in the cellulose derivative is preferably carboxyalkyl or hydroxyalkyl.

Examples of the carboxyalkyl include carboxymethyl, carboxyethyl (1-carboxyethyl and 2-carboxyethyl), carboxypropyl (1-carboxypropyl, 2-carboxypropyl and 3-carboxypropyl), carboxyisopropyl (1-carboxy-2-methylethyl and 2-carboxy-2-methylethyl), carboxybutyl (1-carboxybutyl, 2-carboxybutyl, 3-carboxybutyl and 4-carboxybutyl), carboxy t-butyl, carboxypentyl (1-carboxypentyl, 2-carboxypentyl, 3-carboxypentyl, 4-carboxypentyl and 5-carboxypentyl), carboxyhexyl (1-carboxyhexyl, 2-carboxyhexyl, 3-carboxyhexyl, 4-carboxyhexyl, 5-carboxyhexyl and 6-carboxyhexyl).

Examples of the hydroxyalkyl include hydroxymethyl, hydroxyethyl (1-hydroxyethyl and 2-hydroxyethyl), hydroxypropyl (1-hydroxypropyl, 2-hydroxypropyl and 3-hydroxypropyl), hydroxyisopropyl (1-hydroxy-2-methylethyl and 2-hydroxy-2-methylethyl), hydroxybutyl (1-hydroxybutyl, 2-hydroxybutyl, 3-hydroxybutyl and 4-hydroxybutyl), hydroxy t-butyl, hydroxypentyl (1-hydroxypentyl, 2-hydroxypentyl, 3-hydroxypentyl, 4-hydroxypentyl and 5-hydroxypentyl) and hydroxyhexyl (1-hydroxyhexyl, 2-hydroxyhexyl, 3-hydroxyhexyl, 4-hydroxyhexyl, 5-hydroxyhexyl and 6-hydroxyhexyl).

Specific examples of the cellulose derivative include carboxymethyl cellulose (CMC), hydroxyethyl cellulose (HEC), hydroxypropyl cellulose (HPC) or hydroxypropylmethyl cellulose (HPMC).

The examples of cellulose derivative also include a nanocellulose derivative. The nanocellulose derivative is a derivative of the nanocellulose described below.

The polyvinyl derivative having a hydrophilic group refers to a polyvinyl derivative in which at least one hydrogen atom is substituted with a hydrophilic group, and is preferably a polyvinyl derivative in which at least one hydrogen atom in a methylene unit is substituted with a hydrophilic group. Examples of the hydrophilic group in the polyvinyl derivative include a carbonyl-containing hydrophilic group, a carboxy-containing hydrophilic group, a nitrogen-containing hydrophilic group, and a ring (carbocycle or heterocycle)-containing hydrophilic group. The hydrophilic group in the polyvinyl derivative is preferably the carbonyl-containing hydrophilic group, the nitrogen-containing hydrophilic group, and the heterocycle-containing hydrophilic group, and more preferably a lactam (e.g., α-lactam, β-lactam, γ-lactam, δ-lactam, ε-lactam). Specific examples of the polyvinyl derivative having the hydrophilic group include polyvinylpyrrolidone.

The polyether compound refers to a polymer containing an ether structure in a main chain of a repeat unit. Examples of the polyether compound include a polyalkyleneoxy compound (e.g., poly $C_{1-6}$ alkyleneoxy compound). Examples of the polyalkyleneoxy compound include polyethylene glycol and polypropylene glycol. The polyalkyleneoxy compound is preferably polyethylene glycol.

The nanocellulose is a fibrous cellulose having a fiber width in a nanometer order. The fiber width of the nanocellulose is, for example, 500 nm or less, and may be preferably 200 nm or less, more preferably 100 nm or less, still more preferably 50 nm or less, still further more preferably 10 nm or less, and particularly preferably 5 nm or less.

Examples of the cellulose derivatives, the polyvinyl derivatives with hydrophilic groups and the polyether compounds also include salts thereof. Examples of the salt includes salts of metal (e.g., a monovalent metal such as lithium, sodium, potassium, rubidium and cesium; and a bivalent metal such as calcium, magnesium and zinc), and salts of inorganic base (e.g., ammonia).

The polymer may have a weight-average molecular weight of 10 kDa or more, for example, in order to accomplish the object of the present invention. The weight-average molecular weight of the polymer may be preferably 12 kDa or more, more preferably 14 kDa or more, still more preferably 16 kDa or more, still further more preferably 18 kDa or more, and particularly preferably 20 kDa or more. The weight-average molecular weight of the polymer may be preferably 5000 kDa or less, more preferably 3000 kDa or less, still more preferably 2000 kDa or less, still further more preferably 1000 kDa or less, and particularly preferably 500 kDa or less. More specifically, the weight-average molecular weight of the polymer may be preferably 12 to 5000 kDa, more preferably 14 to 3000 kDa, still more preferably 16 to 2000 kDa, still further more preferably 18 to 1000 kDa, and particularly preferably 20 to 500 kDa.

The polymer concentration in a separation step of the extracellular vesicles is not particularly limited, as long as the extracellular vesicles can be recovered at a higher efficiency than that without containing polymer and the polymer can be dissolved in the solution used in the separation step. Such a concentration varies depending on kinds of polymers, but may be 0.01 to 10.00 wt %, for example, preferably 0.05 to 7.50 wt %, more preferably 0.10 to 5.00 wt %.

In the separation step of the extracellular vesicles, the extracellular vesicles are separated in a liquid phase from the extracellular vesicle-containing sample. That is, the extracellular vesicles are separated from the extracellular vesicle-containing sample without coprecipitating with the polymer by means of a separation method described below. As such, the separation step of the present invention differs from a separation (e.g., polyethylene glycol precipitation) by means of coprecipitation with a coprecipitating polymer. Therefore, the polymer used in the present invention is preferably non-coprecipitating polymer.

In the method of recovering in the present invention, the polymer is present in the separation step. As such, the method of recovering in the present invention may include mixing the extracellular vesicle-containing sample with the polymer. For example, it is possible to separate the extracellular vesicles from the extracellular vesicle-containing sample after mixing the extracellular vesicle-containing sample with the polymer. In addition, for example, in the case of employing a separation method using an extracellular vesicle membrane-binding material described below, it is possible to add the polymer in a solution containing the extracellular vesicle membrane-binding material in advance and then add the extracellular vesicle-containing sample.

The method of recovering in the present invention may further include mixing the extracellular vesicle-containing sample with a chelating agent. In this case, the extracellular vesicles are separated from the extracellular vesicle-containing sample in the presence of the polymer and the chelating agent in the method of recovering according to the present invention. As Such, for example, it is possible to add the polymer and the chelating agent simultaneously to the extracellular vesicle-containing sample, add the chelating agent after the polymer is added to the extracellular vesicle-containing sample, or add the polymer after the chelating agent is added to the extracellular vesicle-containing sample. In addition, for example, in the case of employing the separation method using the extracellular vesicle membrane-binding material described below, it is possible to add the polymer and the chelating agent to the solution containing the extracellular vesicle membrane-binding material in advance and then add the extracellular vesicle-containing sample.

The chelating agent is a compound having a coordination moiety capable of coordinating with a metal ion, or a salt thereof. The number of the coordination moiety(ies) is preferably 2 or more, more preferably 3 or more (e.g., 3 or 6). Examples of the coordination atom as the coordination moiety include an oxygen atom, a phosphorus atom, a nitrogen atom, a sulfur atom and a chlorine atom. The coordination atom is preferably the oxygen atom or the phosphorus atom, and more preferably the oxygen atom. Examples of a coordination group as the coordination moiety include a group having the abovementioned coordination atom. The coordination group is preferably a carboxylic acid group or a phosphoric acid group, and more preferably the carboxylic acid group.

Examples of the chelating agent include oxalic acid, hydroxyethyl iminodiacetic acid (HIDA), nitrilotriacetic acid (NTA), hydroxyethyl ethylenediaminetriacetic acid (HEDTA), ethylenediaminetetraacetic acid (EDTA), ethylenediaminetetra(methylene phosphonic acid) (EDTMP), glycoletherdiaminetetraacetic acid (EGTA), and salts thereof. Examples of the salts include metal salts (e.g., monovalent metal salts such as sodium salts, potassium salts, and bivalent metal salts such as calcium salts, magnesium salts), inorganic salts (e.g., halide salts such as fluoride, chloride, bromide and iodide, and ammonium salts), organic salts (e.g., ammonium salts substituted with an alkyl group), and acid addition salts (e.g., salts with an inorganic acid such as sulfuric acid, hydrochloric acid, hydrobromic acid, nitric acid, phosphoric acid and the like, and salts with an organic acid such as acetic acid, oxalic acid, lactic acid, citric acid, trifluoromethanesulfonic acid, trifluoroacetic acid and the like). In the present invention, a mixture of 2 or more (e.g., 2, 3, 4, or 5) kinds of chelating agents may be used for the separation of the extracellular vesicle-containing sample.

The chelating agent possibly exhibits advantageous effects on the recovering the extracellular vesicles at a high purity by suppressing adsorption of impurities on the extracellular vesicles (International Patent Application Publication No. 2018/070479). As such, the chelating agent exhibits synergetic effects on improvement of the efficiency of recovering the extracellular vesicles by the separation of the extracellular vesicles from the extracellular vesicle-containing sample in the presence of the polymer and the chelating agent. The above chelating agents exhibit advantageous effects on recovering the extracellular vesicles at a high purity, and thereby give comparable synergetic effects in combination use of the polymer.

The concentration of the chelating agent in the step of separating the extracellular vesicles is not particularly limited, as long as suppressing adsorption of impurities on the extracellular vesicles and allowing the chelating agent to be dissolved in the solution used in the separation step. Such a concentration varies depending on kinds of the chelating agent, and is 1 mM to 200 mM, for example. Preferably, the concentration of the chelating agent may be 10 mM or more, 15 mM or more, 20 mM or more, 30 mM or more, 40 mM or more, or 50 mM or more. Such a concentration varies depending on kinds of the chelating agent, and may be 200 mM or less, 180 mM or less, 160 mM or less, 140 mM or less, 120 mM or less, or 100 mM or less.

The separation (step (1)) of extracellular vesicles from the extracellular vesicle-containing sample in the presence of the polymer can be carried out by the separation method using the extracellular vesicle membrane-binding material or ultracentrifugal method. The separation using the extracellular vesicle membrane-binding material can be performed in a process of an analysis method (e.g., immunoassay described below). In the case of separating the extracellular vesicles with use of the extracellular vesicle membrane-binding material, it is possible to recover the extracellular vesicles by mixing the extracellular vesicle-binding material with the extracellular vesicle-containing sample to allow the extracellular vesicle membrane-binding material to bind to the extracellular vesicles and then separating the extracellular vesicle membrane binding material-bound extracellular vesicles from the sample. In the case of separating the extracellular vesicles by the ultracentrifugal method, it is possible to recover the extracellular vesicles by precipitating the extracellular vesicles in the extracellular vesicle-containing sample by the ultracentrifugal method and then discarding supernatant. In the case of separating the extracellular vesicles in the process of the analysis method, it is possible to separate the extracellular vesicles by removing the solution or washing a solid phase in the analysis method (e.g., immunoassay such as ELISA). Specifically, in the immunoassay, it is possible to separate the extracellular vesicles by binding to an antibody of the extracellular vesicle and removing the solution containing the extracellular vesicle-containing sample and/or washing the solid phase. The separation is preferably isolation or purification. Therefore, the method of recovering in the present invention can be utilized as a method of isolation or purification.

The extracellular vesicle membrane-binding material used in the recovering method of the present invention is a material with an affinity to an extracellular vesicle marker. Examples of the extracellular vesicle marker include a tetraspanin membrane protein (extracellular vesicle membrane specific four transmembrane protein, e.g., CD9, CD63 and CD81), an extracellular matrix metalloproteinase inducer (CD147), carcinoembryonic antigen (CEA), heat shock protein (HSP) 70, HSP90, major histocompatibility complex (MHC) I, tumor susceptibility gene (TSG) 101, lysosome associated membrane protein (LAMP) 1, intercellular adhesion molecule (ICAM)-1, integrin, ceramide, cholesterol, phosphatidylserine, ALIX, Annexins, Caveolin-I, Flotillin-I, Rab protein and EpCAM. The extracellular vesicle marker is preferably the tetraspanin membrane protein or the extracellular matrix metalloproteinase inducer. Instead, the extracellular vesicle marker is preferably CD9, CD63, CD81 or CD147. Examples of the extracellular vesicle membrane-binding material include antibodies (e.g., monoclonal antibodies and polyclonal antibodies) and antigen-binding fragments thereof, aptamers, phosphatidylserine-bound proteins, and ceramide-bound proteins. The antigen-binding fragment is an antibody fragment that maintains binding to the targeted extracellular vesicle marker. Examples of the antigen-binding fragment include Fab, Fab', F(ab')$_2$ and scFv. The extracellular vesicle membrane-binding material is preferably the antibody or the antigen-binding fragment thereof, and more preferably monoclonal antibody or its antigen-binding fragment. The extracellular vesicle membrane-binding material(s) used in recovering the extracellular vesicles is used solely or in combination thereof.

The extracellular vesicle membrane-binding material may be bound to the solid phase facilitating the separation of the extracellular vesicles. As the solid phase, it is possible to use sepharose beads, agarose beads, magnetic beads or a plastic plate, for example. The extracellular vesicle membrane-binding material can be immobilized to the solid phase in a conventional method known to a person skilled in the art.

In the recovering method of the present invention, when the extracellular vesicles are recovered by the separation method using the extracellular vesicle membrane-binding material, the polymer is present at least in mixing the extracellular vesicle membrane-binding material with the extracellular vesicle-containing sample. For example, in the case of using the magnetic beads, the extracellular vesicle-containing sample can be mixed in the presence of the polymer with the extracellular vesicle membrane-binding material that is bound to the magnetic beads, making it possible to bind the extracellular vesicle membrane-binding material to the extracellular vesicles in the extracellular vesicle-containing sample. The magnetic beads are magnetically collected with a permanent magnet, an electromagnet or the like. Next, the extracellular vesicles bound to the magnetic beads can be separated from the extracellular vesicle-containing sample by discarding the supernatant that contains components not bound to the magnetic beads. The magnetic beads can be magnetically collected by a method known to a person skilled in the art. For example, in the case of using sepharose beads or agarose beads, the extracellular vesicle-containing sample can be mixed in the presence of the polymer with the extracellular vesicle membrane-binding material that is bound to the beads, making it possible to bind the extracellular vesicle membrane-binding material to the extracellular vesicles in the extracellular vesicle-containing sample. The beads can be precipitated by centrifuge. Then, the extracellular vesicles bound to the beads can be separated from the extracellular vesicle-containing sample by discarding the supernatant that contains components not bound to the beads. The beads can be centrifuged by a method known to a person skilled in the art.

In the case of separating the extracellular vesicles from the extracellular vesicle-containing sample by the separation method using the extracellular vesicle membrane-binding material, a temperature for mixing extracellular vesicle membrane-binding material with the extracellular vesicle-containing sample may be an arbitrary temperature as long as the mixture of extracellular vesicle membrane-binding material with the extracellular vesicle-containing sample is present in a liquid form, or may be 0 to 100° C. Such a temperature is 4° C. or more, for example, and may be preferably 15° C. or more, more preferably 35° C. or more, still more preferably 40° C. or more. Such a temperature is 80° C. or less, for example, and may be preferably 70° C. or less, more preferably 60° C. or less, still more preferably 50° C. or less. More specifically, such a temperature is 4 to 80° C., for example, and may be preferably 15 to 70° C., more preferably 35 to 60° C., still more preferably 40 to 50° C. A time for binding the extracellular vesicle membrane-binding material to the extracellular vesicles is not particularly limited as long as the time is long enough to bind the extracellular vesicle membrane-binding material to the extracellular vesicles, and may be 1 minute or more, 5 minutes or more, 10 minutes or more, or 20 minutes or more. Such a time may be 24 hours or less, 18 hours or less, 8 hours or less, 4 hours or less, 2 hours or less, or 1 hour or less.

In the recovering method of the present invention, in the case of recovering the extracellular vesicles by the ultracentrifugal method, the polymer is present when the extracellular vesicle-containing sample is provided for the ultracentrifugal separation. For example, when ultracentrifugal separation is performed plural times, at least one time of the ultracentrifugal separation is carried out in the presence of the polymer. The ultracentrifugal separation can be performed with use of an ultracentrifuge. Gravitational force applied for the ultracentrifugal separation is 10,000×g to 200,000×g, for example, and may be preferably 70,000×g to 150,000×g. The time for the ultracentrifugal separation is 0.5 to 24 hours, for example, and preferably 1 to 5 hours. The temperature for the ultracentrifugal separation is 4 to 30° C., for example. The ultracentrifugal separation can be carried out one time or plural (e.g., 2 and 3) times.

The present invention also provides the analysis method of the extracellular vesicle(s).

The analysis method of the present invention includes:
(1) separating the extracellular vesicle(s) from the extracellular vesicle-containing sample; and
(2) analyzing the separated extracellular vesicle(s).

The step (1) in the analysis method of the present invention can be carried out in the same way as in the step (1) in the recovering method of the present invention.

In the step (2), the separated extracellular vesicle is analyzed. Examples of an object to be analyzed include components contained in the extracellular vesicle (components contained inside the extracellular vesicle, membrane components of the extracellular vesicle, and components present on a surface of the extracellular vesicle membrane) and the extracellular vesicle itself (particle).

For the analysis of the components contained inside the extracellular vesicle, the analysis refers to detection or quantification of the components. Such an analysis refers to an analysis of one component or plural components. Examples of the components to be analyzed include proteins, nucleic acids (e.g., RNA and DNA), saccharides, lipids, amino acids, vitamins, polyamines and peptides. The recovering amount of the extracellular vesicles can be increased by the separation of the extracellular vesicles from the extracellular vesicle-containing sample in the presence of the polymer. Accordingly, the analysis method of the present invention enables highly precise analysis of the components of proteins, nucleic acids and the like in the extracellular vesicles.

The component analysis can be performed by any well-known method in the relevant field.

In the case that the component to be analyzed is a protein, examples of the analysis method include immunoassay and mass spectrometry. Examples of the immunoassay include a direct competitive method, an indirect competitive method and a sandwich method. Also, examples of such an immunoassay include chemiluminescent immunoassay (CLIA) [e.g., a chemiluminescent enzyme immunoassay (CLEIA)], turbidimetric immunoassay (TIA), enzyme immunoassay (EIA) (e.g., direct competitive ELISA, indirect competitive ELISA, and sandwich ELISA), radioimmunoassay (RIA), latex agglutination reaction method, fluorescence immunoassay (FIA), and immunochromatography, Western blotting, immunostaining and fluorescence activated cell sorting (FACS). In the case of detecting multiple components, proteomic analysis may be performed.

In the case that the component to be analyzed is a nucleic acid, examples of the analysis method include hybridization methods using probes, reverse transcription (RT) reactions using reverse transcriptase, gene amplification methods (e.g., PCR methods such as quantitative PCR, RT-PCR) using primer (2, 3 or 4 primers), sequencing and mass spectrometry.

In the case that the component to be analyzed is a component other than a protein or a nucleic acid, examples of the analysis method include immunoassay and mass spectrometry. In the case of analyzing multiple components, metabolome analysis can be performed.

The analysis method of the present invention can be used for detection of the marker contained in the extracellular vesicle. Examples of the marker contained in the extracellular vesicle include markers as indicators of the extracellular vesicle, and markers as indicators of diseases such as cancer (e.g., diagnosis markers and evaluation markers of disease risk). Examples of the marker of the extracellular vesicle include the tetraspanin membrane protein (extracellular vesicle membrane specific four transmembrane protein, e.g., CD9, CD63 and CD81), the extracellular matrix metalloproteinase inducer (CD147), the carcinoembryonic antigen (CEA), the heat shock protein (HSP) 70, HSP90, the major histocompatibility complex (MHC) I, the tumor susceptibility gene (TSG) 101, the lysosome associated membrane protein (LAMP) 1, the intercellular adhesion molecule (ICAM)-1, integrin, ceramide, cholesterol, phosphatidylserine, ALIX, Annexins, Caveolin-I, Flotillin-I, Rab protein, EpCAM and nucleic acids (e.g., DNA and RNA) encoding proteins thereof. Examples of the marker as indicator of disease include proteins (referred to as "abnormal protein", hereinafter, e.g., mutant protein and extrinsic protein) that are present specifically in the extracellular vesicles derived from living things suffering from diseases such as cancer or extracellular vesicles secreted from abnormal cells such as cancer cells. Examples of the mutant protein include fusion proteins such as EML4-ALK. There are variants such as variants 1, 2, 3a, 3b, 4, 5a, 5b and 6 in EML4-ALK. Examples of the extrinsic protein include virus-derived proteins. Examples of the marker as indicator of disease also include presence and absence of expression of nucleic acids encoding these proteins, change of amounts thereof, mutants such as SNP, haplotype, transposition, presence and absence of methylation of nucleic acid and kinds of variant.

Analysis of the extracellular vesicle itself (particle) can be performed with equipment such as particle analysis equipment, electron microscope and flow cytometer, for example. In this case, it is possible to analyze the number, dimension, shape of particles of the extracellular vesicle and distribution thereof.

There are reports regarding extracellular vesicle possibly relevant to various diseases such as cancer (International Patent Application Publication No. 2014/003053; International Patent Application Publication No. 2014/152622; and Taylor et al., Gynecologic Oncol., 100 (2008) pp 13-21). As such, the recovering method and the analysis method of the present invention are useful in diagnosis based on the extracellular vesicle and drug development. For example, the detection of EML4-ALK functioning as the marker of cancer such as lung cancer according to the analysis method of the present invention can be useful as an indicator for determination of administration of ALK tyrosine kinase inhibitor such as crizotinib and alectinib.

In another embodiment, the present invention provides the analysis method of the extracellular vesicle(s) including the following:
 (1) separating the extracellular vesicle(s) from the extracellular vesicle-containing sample with the extracellular vesicle membrane-binding material; and
 (2) analyzing the marker that is contained in the separated extracellular vesicle(s) and functions as the indicator of disease such as cancer.

Examples of the extracellular vesicle membrane-binding material in the present embodiment include the material with an affinity to the above extracellular vesicle marker. The extracellular vesicle marker is preferably the tetraspanin membrane protein and the extracellular matrix metalloproteinase inducer. As well, the extracellular vesicle marker is preferably CD9, CD63, CD81 or CD147, and more preferably CD9 or CD63. Examples of the extracellular vesicle membrane-binding material include the above antibodies (e.g., monoclonal antibodies and polyclonal antibodies) and antigen-binding fragments thereof, aptamers, phosphatidylserine-bound proteins, and ceramide-bound proteins.

Examples of the marker as indicator of disease such as cancer include presence and absence of expression of the above abnormal proteins and change of amounts thereof. Examples of the abnormal protein include the fusion protein such as EML4-ALK. Examples of the marker as indicator of disease also include presence and absence of expression of nucleic acids encoding these proteins, change of amounts thereof, mutants such as SNP, haplotype, transposition, presence and absence of methylation of nucleic acid and kinds of variant.

The present invention also provides a kit that includes the polymer and the extracellular vesicle membrane-binding material described above. The kit of the present invention can further include the chelating agent. The kit of the present invention is useful, for example, for simple implementation of the recovering method and the analysis method of the present invention.

EXAMPLES

Hereinafter, the present invention will be described with reference to Examples, but the present invention is not limited to these Examples.

Example 1

The effect on EV recovery was investigated for three kinds of commercially available CMC sodium salts (hereinafter referred to as "CMC". CAS No. 9004-32-4, Nacalai Tesque, Inc. #07326-95 (unknown average molecular weight); Sigma-Aldrich Co. LLC #C5678 (average molecular weight 90 kDa); #C4888 (average molecular weight 250 kDa)). EV recovery was performed using the anti-CD9 antibody.

Healthy human serum was centrifuged at 20,000×g at 4° C. for 15 minutes, then 200 μL of the serum was diluted with 200 μL of PBS (2.9 mM $NaH_2PO_4$, 9.0 mM $Na_2HPO_4$, 137 mM NaCl), EDTA/EGTA-PBS (PBS containing EDTA and EGTA with a final concentration of 50 mM after the dilution of the serum, respectively) (ED/EG), or CMC-PBS with a final concentration of 0.2 to 2.5 wt % (PBS in which CMC was dissolved to have a final concentration of 0.2 to 2.5 wt % after the dilution of the serum). Then, magnetic beads (Dynabeads M-280 tosylactivated (Life Technologies)) to which an anti-CD9 antibody (our product) is attached, was added to the resultant solution to achieve 0.26 mg/mL. After the resultant solution underwent reaction at 4° C. while rotated overnight, the magnetic beads were washed three times with PBS-T, then diluted with a sample buffer (Bio-Rad Laboratories, Inc.) for preparation of a western blotting sample. In the western blotting sample, a sample containing exosomes was treated with SDS to disrupt the exosomes for releasing a marker protein (e.g., CD9) of the exosomes in the sample solution. Immunoprecipitation efficiency was analyzed by western blotting method with use of a biotinylated anti-CD9 antibody (our product) (FIG. 1). Improvement of EV recovery efficiency was recognized for all of four CMC, compared to PBS-diluted samples.

Table 1 is a list of physical properties of CMC used in the Example.

TABLE 1

List of CMC used in Example

| Product code | Source | Average molecular weight (kDa) | Viscosity/measurement condition (Values disclosed by manufacturer) |
|---|---|---|---|
| #07326-95 | Nacalai Tesque, Inc. | No data | No data |
| #C5678 | Sigma-Aldrich Co. LLC | Average Mw 90 | 50 to 200 mPa · s/ 4 wt % aqueous solution (25° C.) |
| #C4888 | Sigma-Aldrich Co. LLC | Average Mw 250 | 400 to 800 mPa · s/ 2 wt % aqueous solution (25° C.) (lit.) |

Example 2

The effect on EV recovery was investigated for different concentrations (final concentration: 0.06 wt % to 1.0 wt %)

of CMC (Sigma-Aldrich Co. LLC #C4888) at different reaction temperatures (4° C. and 37° C.)

Figure 2:
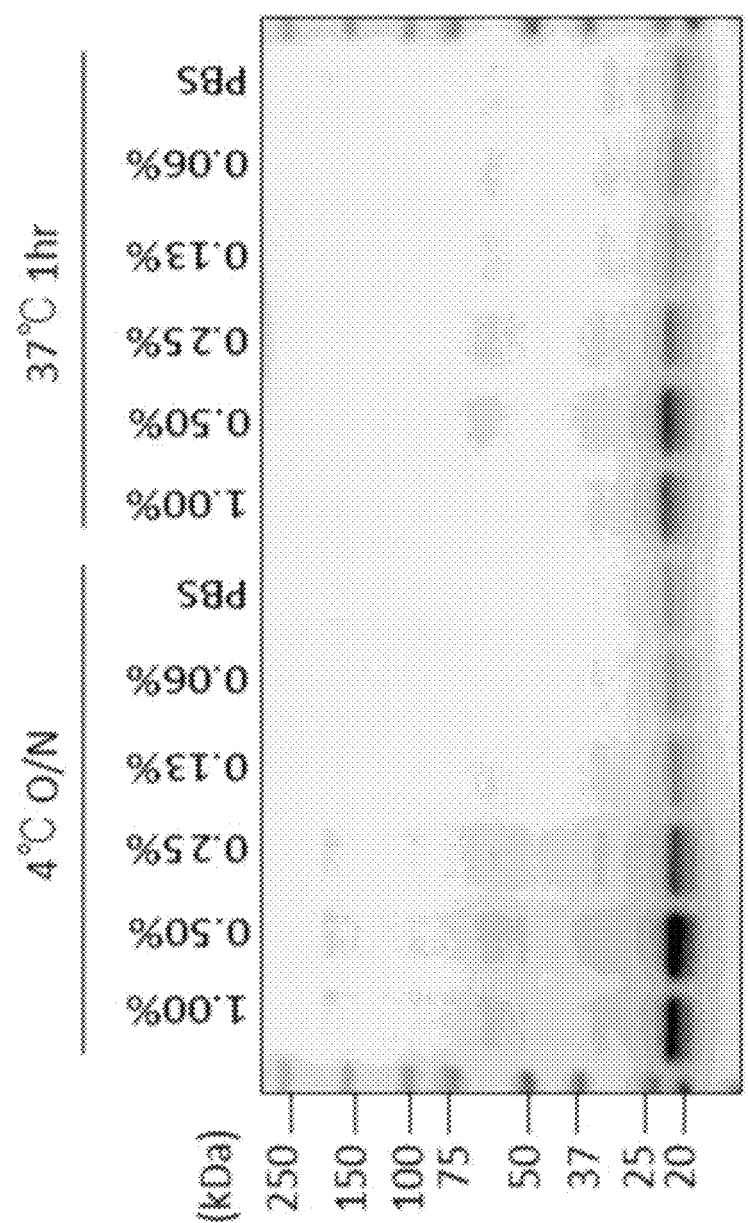
FIG. 2 is a diagram depicting results of a western blotting with a biotinylated anti-CD9 antibody of samples that are obtained by immunoprecipitating a serum specimen diluted with PBS or different concentrations of CMC-PBS together with an anti-CD9 antibody at 4° C. overnight or at 37° C. for one hour, in Example 2.

Healthy human serum was centrifuged at 20,000×g at 4° C. for 15 minutes, then 200 µL of the serum was diluted with 200 µL of PBS or CMC-PBS (PBS in which CMC was dissolved to have a final concentration of 0.06 to 1.0 wt % after the dilution of the serum). Then, magnetic beads (Dynabeads M-280 tosylactivated (Life Technologies)) to which the anti-CD9 antibody (our product) is attached, was added to the resultant solution to achieve 0.26 mg/mL. After the resultant solution underwent reaction while rotated at 4° C. overnight or at 37° C. for 1 hour, the magnetic beads were washed three times with PBS-T, then diluted with the sample buffer (Bio-Rad Laboratories, Inc.) for preparation of the western blotting sample. Recovering efficiency of EV was analyzed by western blotting method with use of the biotinylated anti-CD9 antibody (FIG. 2). Improvement of EV recovery efficiency was recognized in the CMC final concentrations of 0.25 wt % to 1 wt % at the reaction temperatures of 4° C. and 37° C., compared to the PBS-diluted samples.

Example 3

The effect on EV recovery was investigated for CMC (Sigma-Aldrich Co. LLC #C4888) by nanoparticle tracking analysis (NanoSight LM10, Quantum Design, Inc.).

Figure 3:
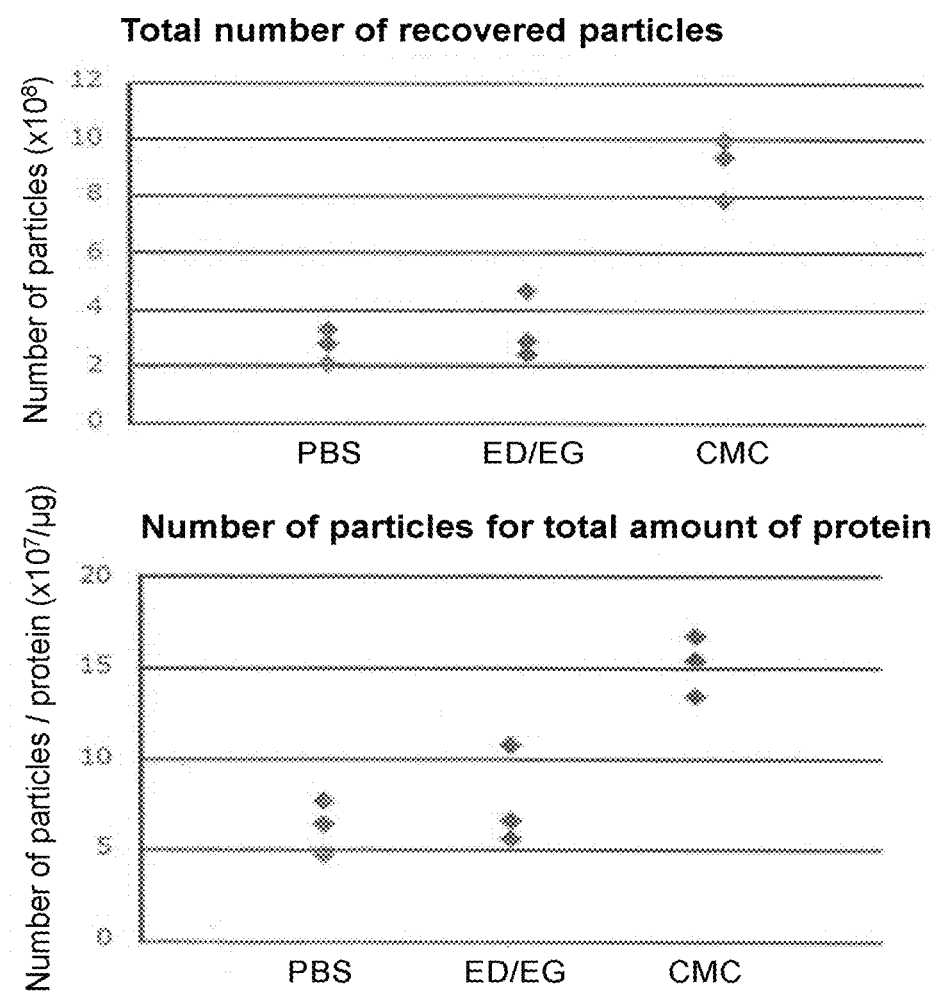
FIG. 3 is a graph representing results of particle count measurements according to nanoparticle tracking analysis of a sample that is obtained from an immunoprecipitation method using an anti-CD9 antibody for a serum specimen diluted with PBS, EDTA/EGTA-PBS ("ED/EG") or CMC-PBS in Example 3.

200 µL of healthy human serum was centrifuged at 20,000×g at 4° C. for 15 minutes, then the resultant supernatant was diluted with 200 µL of PBS, EDTA/EGTA-PBS (PBS containing EDTA and EGTA with a final concentration of 50 mM after the dilution of the serum, respectively) (ED/EG), or CMC-PBS (PBS in which CMC was dissolved to have a final concentration of 0.5 wt % after the dilution of the serum) (CMC). Then, the magnetic beads (Dynabeads M-280 tosylactivated (Life Technologies)) to which the anti-CD9 antibody (our product) is attached, was added to the resultant solution to achieve 0.26 mg/mL. After the resultant solution underwent reaction while rotated at 37° C. for 30 minutes, the magnetic beads were washed three times with PBS-T, then reacted with 40 µL of Britton & Robinson Universal Buffer (BRUB) (pH 2.6) for 5 minutes, and then neutralized with 20 µL of 1M Tris-HCl (pH 8.0) to separate the extracellular vesicles from the antibody magnetic beads. After total protein concentration was determined by Qubit protein assay (Life Technologies), 450 µL of PBS was added for the analysis of the number of particles using NanoSight (FIG. 3). The increase in the total number of recovered particles of EV and the number of particles for total amount of protein was recognized under the dilution of CMC, demonstrating that the extracellular vesicles was recovered at a high purity.

Example 4

The effect on EV recovery of CMC (Sigma-Aldrich Co. LLC #C4888) was investigated for the serum and a plasma that contains each of five kinds of anticoagulants (heparin, EDTA, citrate, acid-citrate-dextrose (ACD) and citrate-phosphate-dextrose (CPD)).

Figure 4:
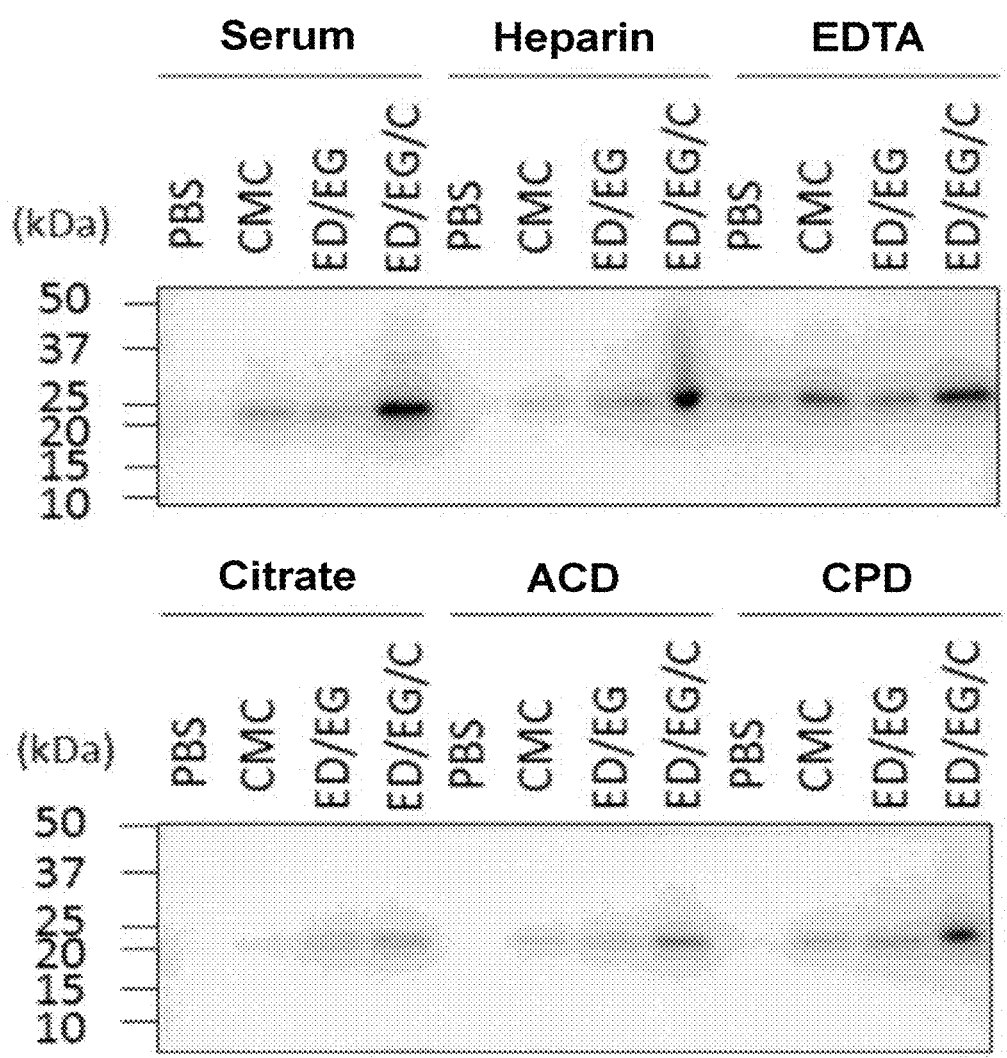
FIG. 4 is a diagram depicting results of a western blotting with a biotinylated anti-CD9 antibody of samples obtained from an immunoprecipitation method using an anti-CD9 antibody for a specimen that is obtained by diluting a serum and a plasma containing each of five kinds of anticoagulants (heparin, EDTA, citrate, acid-citrate-dextrose (ACD) and citrate-phosphate-dextrose (CPD)) with PBS, CMC-PBS, EDTA/EGTA-PBS ("ED/EG") or EDTA/EGTA/CMC-PBS ("ED/EG/C"), in Example 4.

200 µL of the healthy human serum and the anticoagulant-containing healthy human plasma was centrifuged at 20,000×g at 4° C. for 15 minutes, then the resultant supernatant was diluted with 200 µL of PBS, EDTA/EGTA-PBS (PBS containing EDTA and EGTA with a final concentration of 50 mM after the dilution of the serum or plasma, respectively) (ED/EG), or CMC-PBS (PBS in which CMC was dissolved to have a final concentration of 0.5 wt % after the dilution of the serum or plasma) (CMC), or EDTA/EGTA/CMC-PBS (PBS that contains EDTA, EGTA and CMC at a final concentration of 37.5 mM/37.5 mM/0.5 wt % after the dilution of the serum or plasma) (ED/EG/C). Then, magnetic beads (Dynabeads M-280 tosylactivated (Life Technologies)) to which the anti-CD9 antibody (our product) is attached, was added to the resultant solution to achieve 0.26 mg/mL. After the resultant solution underwent reaction while rotated at 37° C. for 1 hour, the magnetic beads were washed three times with PBS-T, then diluted with the sample buffer (Bio-Rad Laboratories, Inc.) for preparation of the western blotting sample. Immunoprecipitation efficiency was analyzed by western blotting method with use of the biotinylated anti-CD9 antibody (FIG. 4). Improvement of EV recovery efficiency using CMC was recognized also for the plasma samples regardless of kinds of the anticoagulants. Further improvement of EV recovery efficiency was recognized in combination use of CMC and the chelating agent.

Example 5

The effect on EV recovery of CMC (Sigma-Aldrich Co. LLC #C4888) using antibodies against two kinds of tetraspanin membrane proteins (CD63 and CD81) other than CD9 and against an extracellular matrix metalloproteinase inducer (CD147).

Figure 5A:
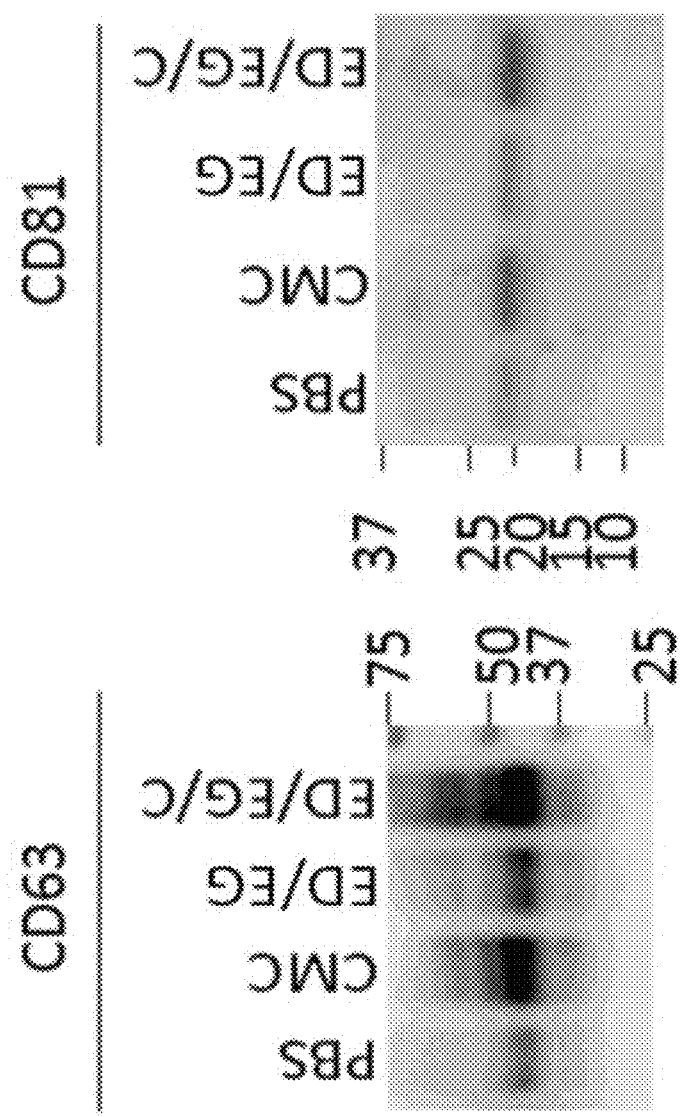
FIG. 5A is a diagram depicting results of a western blotting with an anti-tetraspanin membrane protein antibody (anti-CD63 antibody and anti-CD81 antibody) of samples obtained from an immunoprecipitation method using an anti-tetraspanin membrane protein antibody (anti-CD63 antibody and anti-CD81 antibody) for a serum specimen diluted with PBS, CMC-PBS, EDTA/EGTA-PBS ("ED/EG") or EDTA/EGTA/CMC-PBS ("ED/EG/C"), in Example 5.
Figure 5B:
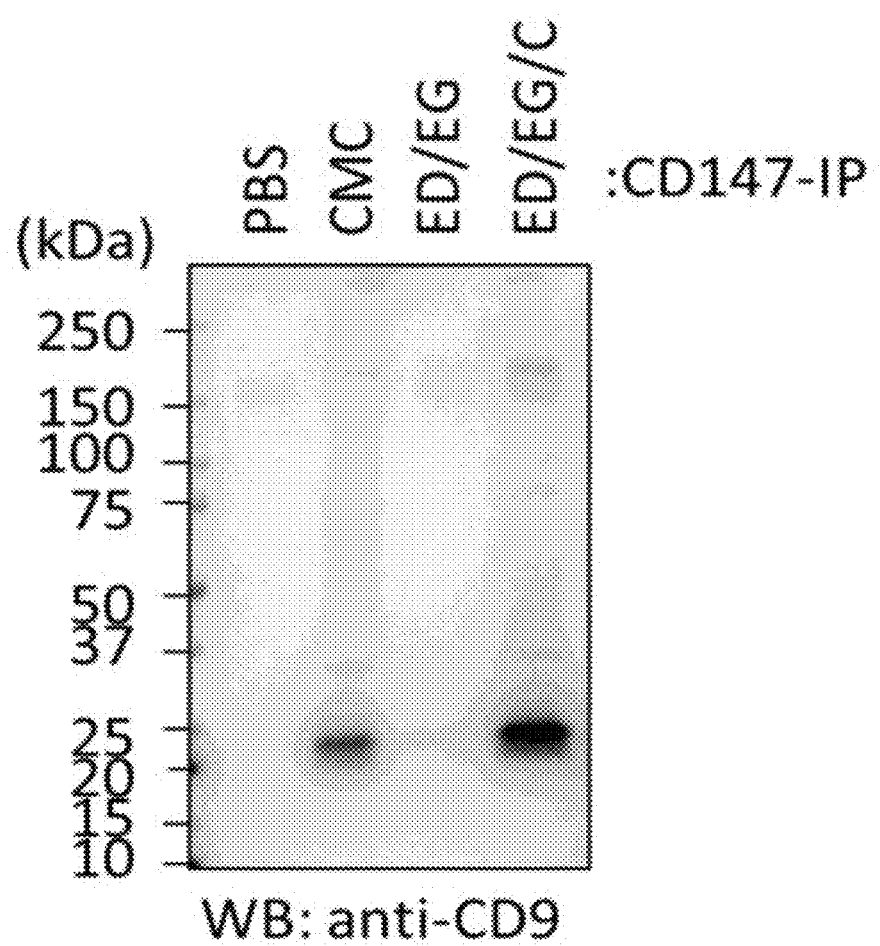
FIG. 5B is a diagram depicting results of a western blotting with a biotinylated anti-CD9 antibody of samples obtained from an immunoprecipitation method using an anti-CD147 antibody for a serum specimen diluted with PBS, CMC-PBS, EDTA/EGTA-PBS ("ED/EG") or EDTA/EGTA/CMC-PBS ("ED/EG/C"), in Example 5.

200 µL of the healthy human serum was centrifuged at 20,000×g at 4° C. for 15 minutes, then the resultant supernatant was diluted with 200 µL of PBS, EDTA/EGTA-PBS (final concentration of 50 mM after the dilution of the serum, respectively) (ED/EG), CMC-PBS (final concentration of 0.5 wt % after the dilution of the serum) (CMC), or EDTA/EGTA/CMC-PBS (with final concentrations of 37.5 mM/37.5 mM/0.5 wt % after the dilution of the serum, respectively) (ED/EG/C). Then, the magnetic beads (Dynabeads M-280 tosylactivated (Life Technologies)) to which the anti-CD63 antibody (8A12: Cosmo Bio Co., Ltd.), the anti-CD81 antibody (M38: Abcam) or the anti-CD147 antibody (MEM-M6/1: Abcam) is attached, are added to the resultant solution to achieve 0.26 mg/mL. After the resultant solution underwent reaction while rotated at 4° C. overnight, the magnetic beads were washed three times with PBS-T, then diluted with the sample buffer (Bio-Rad Laboratories, Inc.) for preparation of the western blotting sample. The EV recovery efficiency was analyzed by western blotting method with use of the anti-CD63 antibody (our product), the anti-CD81 antibody (12C4: Cosmo Bio Co., Ltd.) and the biotinylated anti-CD9 antibody (our product) (FIG. 5A and FIG. 5B). Improvement of EV recovery efficiency using CMC was recognized also in the case of using the antibodies against CD63, CD81 and CD147. Further improvement of EV recovery efficiency was recognized in combination use of CMC and the chelating agent.

Example 6

The effect on EV recovery of CMC (Sigma-Aldrich Co. LLC #C4888) using two kinds of body fluid (urea and saliva) was investigated.

200 µL of the healthy human urea or saliva (two samples that are referred to as "#1" and "#2", respectively) was centrifuged at 15,000×g at 4° C. for 15 minutes. After filtered through 0.22 µm filter, the resultant solution was diluted with 200 µL of PBS, EDTA/EGTA-PBS (final concentration of 50 mM after the dilution of urine or saliva)

Figure 6:
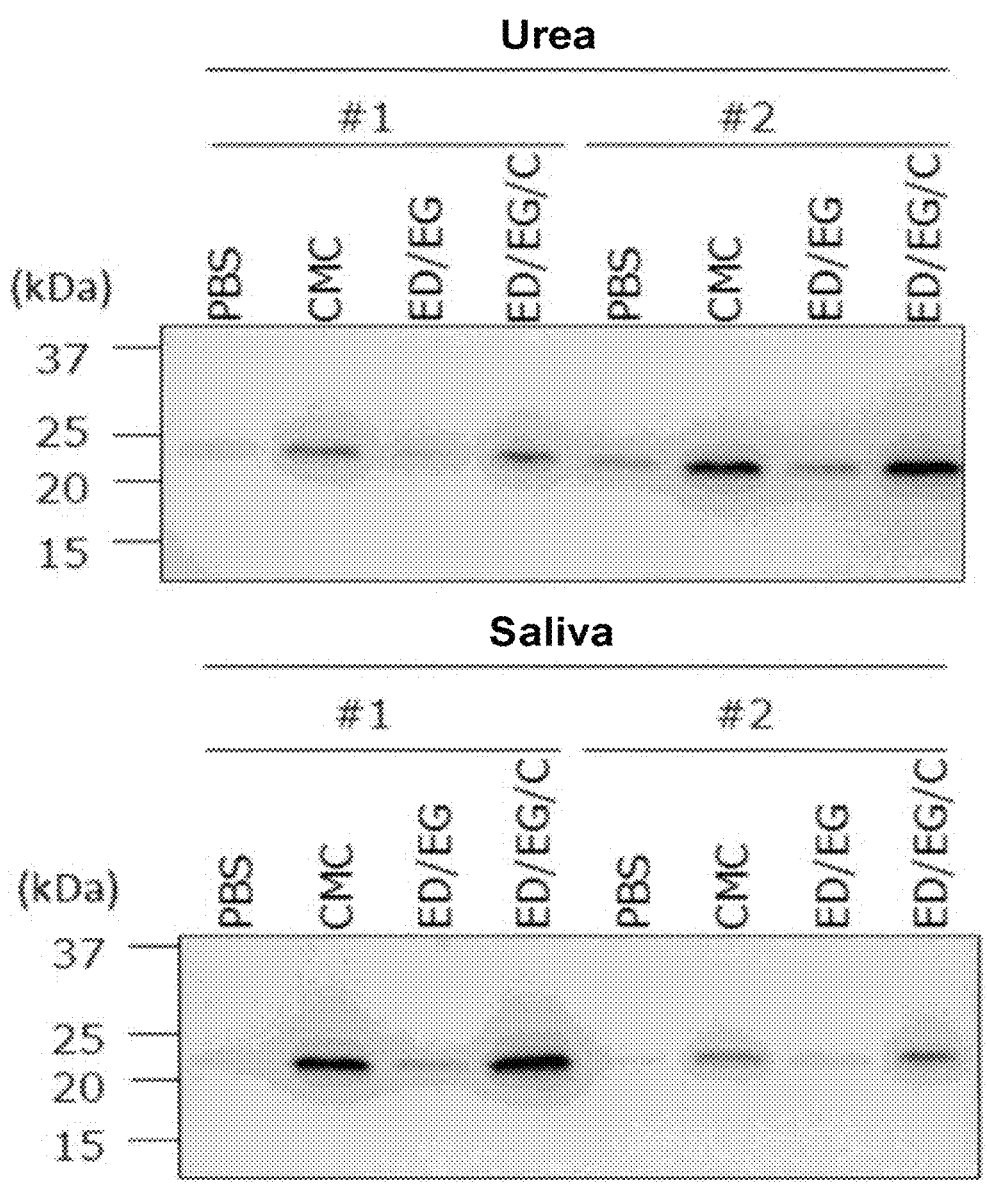
FIG. 6 is a diagram depicting results of a western blotting with a biotinylated anti-CD9 antibody of samples obtained from an immunoprecipitation method using an anti-CD9 antibody for a specimen that is obtained by diluting a body fluid (urine and saliva, for each of which two samples are used, that are represented as "#1" and "#2" respectively) with PBS, CMC-PBS, EDTA/EGTA-PBS ("ED/EG") or EDTA/EGTA/CMC-PBS ("ED/EG/C"), in Example 6.

(ED/EG), CMC-PBS (final concentration of 0.5 wt % after the dilution of urine or saliva) (CMC), or EDTA/EGTA/CMC-PBS (final concentrations of 37.5 mM/37.5 mM/0.5 wt % after the dilution of urine or saliva, respectively) (ED/EG/C). Then, the magnetic beads (Dynabeads M-280 tosylactivated (Life Technologies)) to which the anti-CD9 antibody (our product) is attached, are added to the resultant solution to achieve 0.26 mg/mL. After the resultant solution underwent reaction while rotated at 37° C. for one hour, the magnetic beads were washed three times with PBS-T, then diluted with the sample buffer (Bio-Rad Laboratories, Inc.) for preparation of the western blotting sample. The immunoprecipitation efficiency was analyzed by western blotting method with use of the biotinylated anti-CD9 antibody (FIG. 6). Improvement of EV recovery efficiency using CMC was recognized also for urine and saliva as well as serum and plasma.

Example 7

The effect on EV recovery of cellulose derivatives (0.13 wt % to 4.0 wt % at final concentration) shown below in Table 2.

Figure 7A:
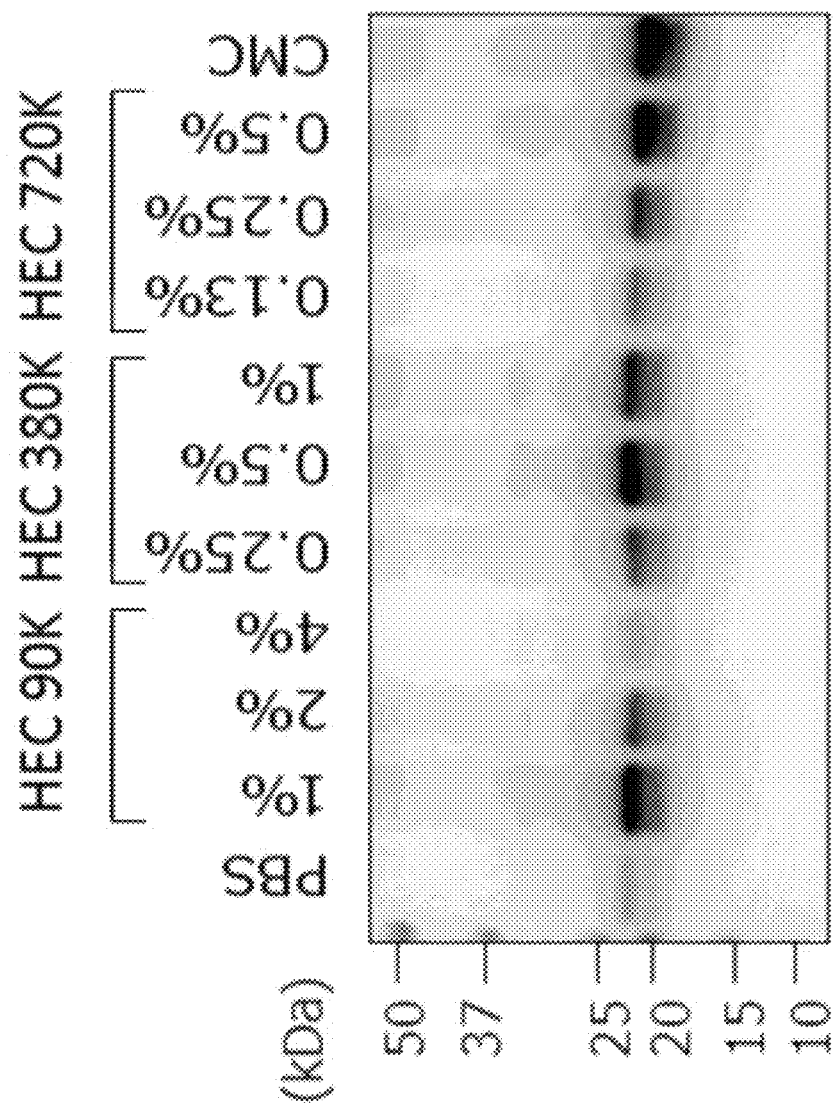
FIG. 7A is a diagram depicting results of a western blotting with a biotinylated anti-CD9 antibody of samples obtained from an immunoprecipitation method using an anti-CD9 antibody for a serum specimen that is diluted with PBS, each of various HEC-PBS at different concentrations, or CMC-PBS in Example 7.
Figure 7B:
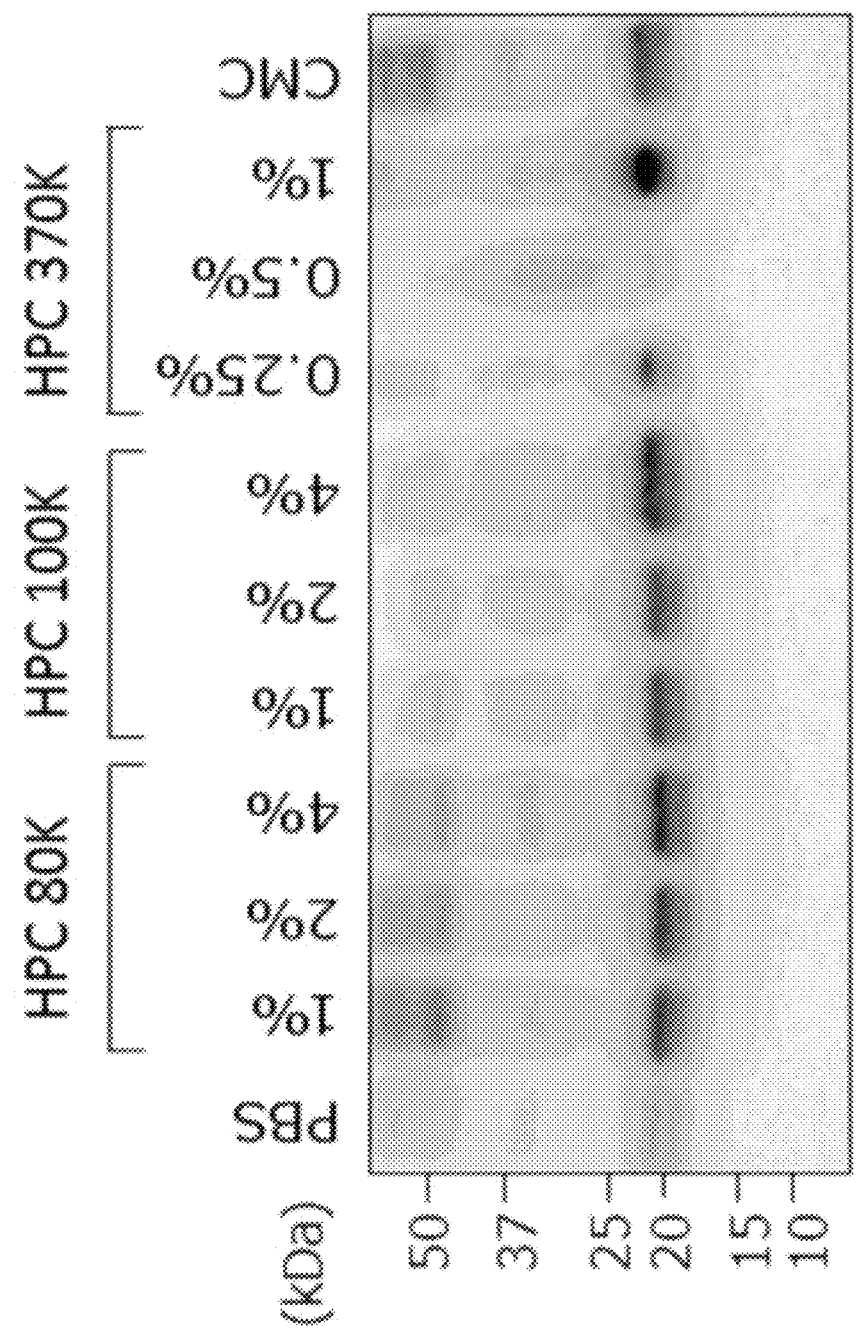
FIG. 7B is a diagram depicting results of a western blotting with a biotinylated anti-CD9 antibody of samples obtained from an immunoprecipitation method using an anti-CD9 antibody for a serum specimen that is diluted with PBS, each of various HPC-PBS at different concentrations, or CMC-PBS in Example 7.
Figure 7C:
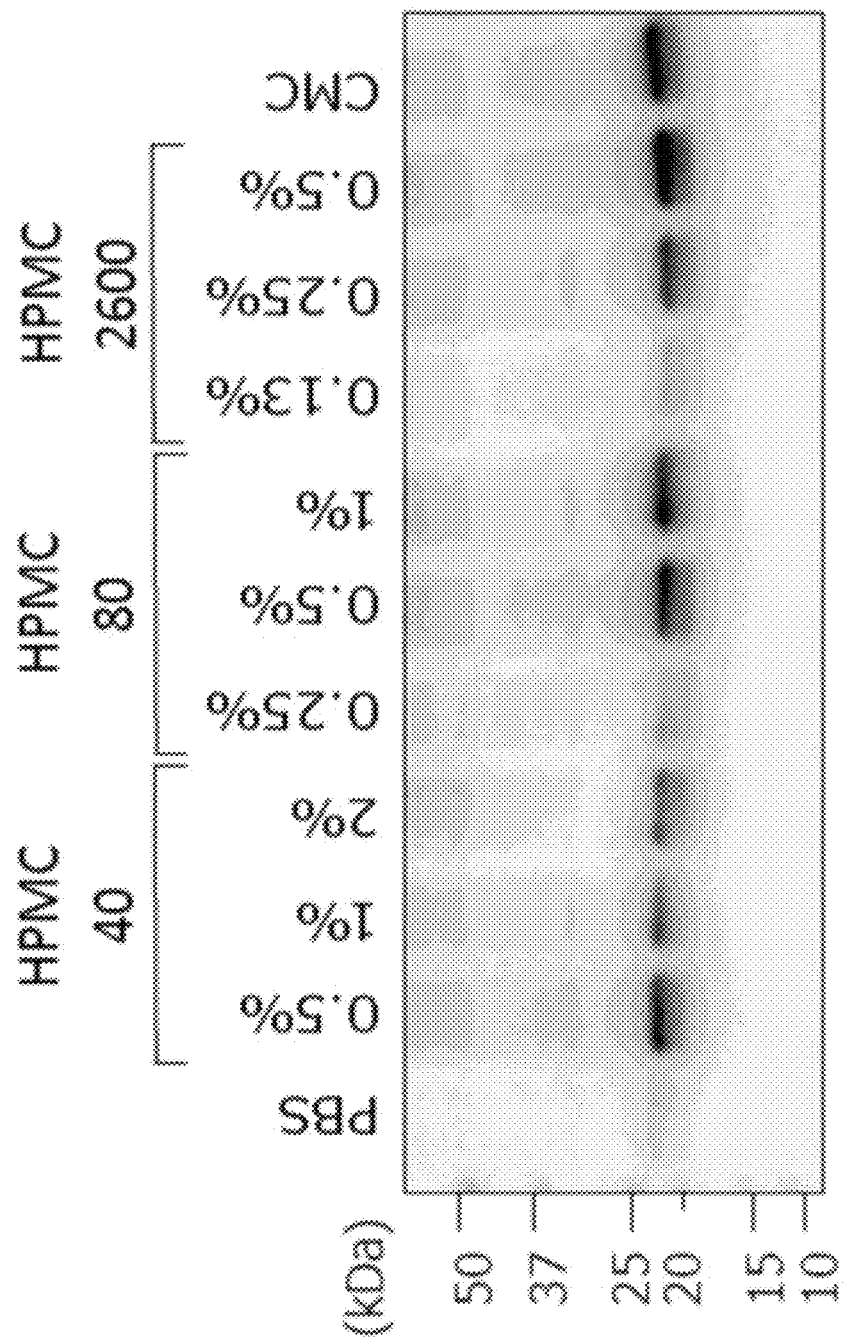
FIG. 7C is a diagram depicting results of a western blotting with a biotinylated anti-CD9 antibody of samples obtained from an immunoprecipitation method using an anti-CD9 antibody for a serum specimen that is diluted with PBS, each of various HPMC-PBS at different concentrations, or CMC-PBS in Example 7.

The healthy human serum was centrifuged at 20,000×g at 4° C. for 15 minutes, then 200 μL of the serum was diluted with 200 μL of PBS, CMC-PBS (final concentration of 0.5 wt % after the dilution of the serum) (CMC), or cellulose derivatives (final concentration of 0.13 to 4.0 wt % after the dilution of the serum) dissolved in PBS. Then, the magnetic beads (Dynabeads M-280 tosylactivated (Life Technologies)) to which the anti-CD9 antibody (our product) is attached, are added to the resultant solution to achieve 0.26 mg/mL. After the resultant solution underwent reaction while rotated at 37° C. for one hour, the magnetic beads were washed three times with PBS-T, then diluted with the sample buffer (Bio-Rad Laboratories, Inc.) for preparation of the western blotting sample. The EV recovery efficiency was analyzed by western blotting method with use of the biotinylated anti-CD9 antibody (FIGS. 7A to 7C). Improvement of EV recovery efficiency was recognized also in the case of using three kinds of cellulose derivative other than CMC, compared to the PBS-diluted samples (0.13 wt % to 2.0 wt % for HEC, 0.25 wt % to 4.0 wt % for HPC, and 0.25 wt % to 2.0 wt % for HPMC).

TABLE 2

List of cellulose derivatives used in Examples (The manufacturer is Sigma-Aldrich Co. LLC for all derivatives.)

| Cellulose derivatives | Product name | Average molecular weight (kDa) | Viscosity/Measurement condition (Values disclosed by manufacturer) |
|---|---|---|---|
| Hydroxyethyl cellulose (HEC) CAS No. 9004-62-0 | HEC 90 kDa #434965 | Average Mv ~90 | 75 to 150 mPa · s/ 5 wt % aqueous solution (25° C.) (lit.) |
| | HEC 380 kDa #308633 | Average Mv ~380 | 300 to 400 mPa · s/ 2 wt % aqueous solution (25° C.) |
| | HEC 720 kDa #434973 | Average Mv ~720 | 4500 to 6500 mPa · s/ 2 wt % aqueous solution (25° C.) (lit.) |
| Hydroxypropyl cellulose (HPC) CAS No. 9004-64-2 | HPC 80 kDa #435007 | Average Mn ~10 Average Mw ~80 | 250 to 800 mPa · s/ 10 wt % aqueous solution (25° C.) (lit.) |
| | HPC 100 kDa #191884 | Average Mw ~100 | 75 to 150 mPa · s/ 5 wt % aqueous solution (25° C.) (lit.) |

TABLE 2-continued

List of cellulose derivatives used in Examples (The manufacturer is Sigma-Aldrich Co. LLC for all derivatives.)

| Cellulose derivatives | Product name | Average molecular weight (kDa) | Viscosity/Measurement condition (Values disclosed by manufacturer) |
|---|---|---|---|
| | HPC 370 kDa #191892 | Average Mw ~370 | 150 to 400 mPa · s/ 2 wt % aqueous solution (25° C.) (lit.) |
| Hydroxypropyl methylcellulose (HPMC) CAS No. 9004-65-3 | HPMC 40-60 cP #H8384 | Average Mw ~22 | 40 to 60 mPa · s/ 2 wt % aqueous solution (20° C.) (lit.) |
| | HPMC 80-120 cP #H9262 | Average Mw ~26 | 80 to 120 mPa · s/ 2 wt % aqueous solution (20° C.) (lit.) |
| | HPMC 2600-5600 cP #H7509 | Average Mw ~86 | 2600 to 5600 mPa · s/ 2 wt % aqueous solution (20° C.) (lit.) |

Example 8

The effect of polyvinylpyrrolidone (1 wt %, 2 wt % and 4 wt % at final concentrations) shown below in Table 3 on the EV recovery was investigated.

Figure 8:
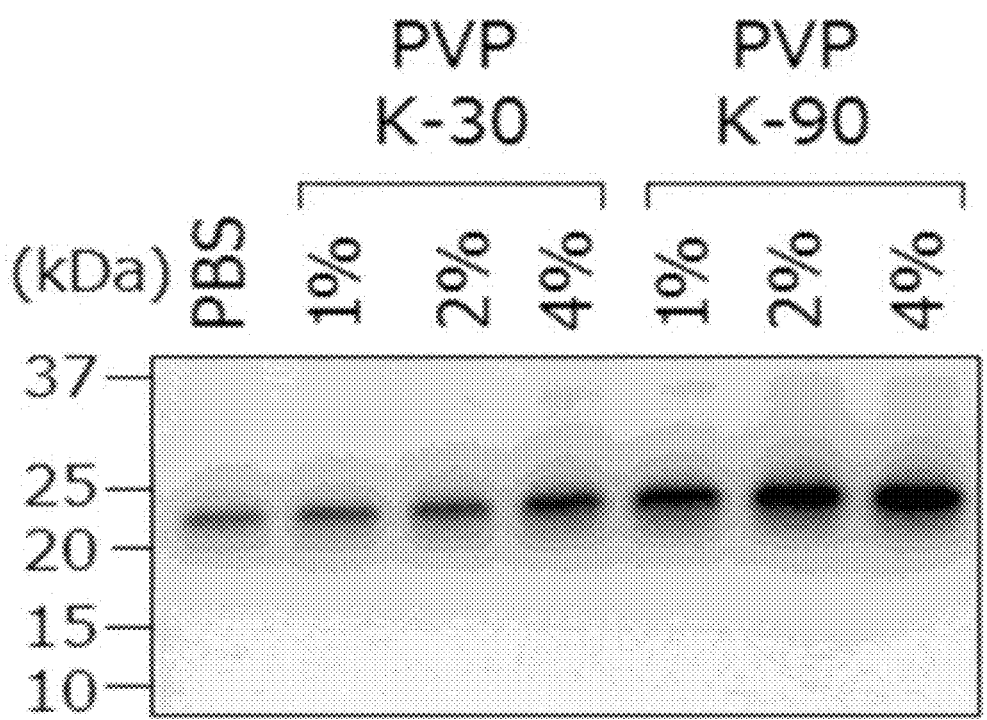
FIG. 8 is a diagram depicting results of a western blotting with a biotinylated anti-CD9 antibody of samples obtained from an immunoprecipitation method using an anti-CD9 antibody for a serum specimen that is diluted with PBS or each of various PVP-PBS at different concentrations, in Example 8.

The healthy human serum was centrifuged at 20,000×g at 4° C. for 15 minutes, then 200 μL of the serum was diluted with 200 μL of PBS, or polyvinylpyrrolidone (final concentration of 1.0 to 4.0 wt % after the dilution of the serum) dissolved in PBS. Then, the magnetic beads (Dynabeads M-280 tosylactivated (Life Technologies)) to which the anti-CD9 antibody (our product) is attached, are added to the resultant solution to achieve 0.26 mg/mL. After the resultant solution underwent reaction while rotated at 37° C. for one hour, the magnetic beads were washed three times with PBS-T, then diluted with the sample buffer (Bio-Rad Laboratories, Inc.) for preparation of the western blotting sample. The EV recovery efficiency was analyzed by western blotting method with use of the biotinylated anti-CD9 antibody (FIG. 8). Improvement of EV recovery efficiency was recognized for polyvinylpyrrolidone in a range of 1.0 wt % to 4.0 wt %, compared to the PBS-diluted samples.

TABLE 3

List of polyvinylpyrrolidone (PVP) used in Examples

| Polyvinyl derivatives | Product name | Manufacturer | Average molecular weight (kDa) |
|---|---|---|---|
| polyvinylpyrrolidone (PVP) CAS No. 9003-39-8 | PVP K-30 28314-82 nacalai | Nacalai Tesque, Inc. | Mw 40 |
| | PVP K-90 28315-72 nacalai | Nacalai Tesque, Inc. | Mw 360 |

Example 9

The effect on the EV recovery was investigated under different reaction temperatures ranging from 35° C. to 60° C. for CMC (Sigma-Aldrich Co. LLC #C4888).

Figure 9A:
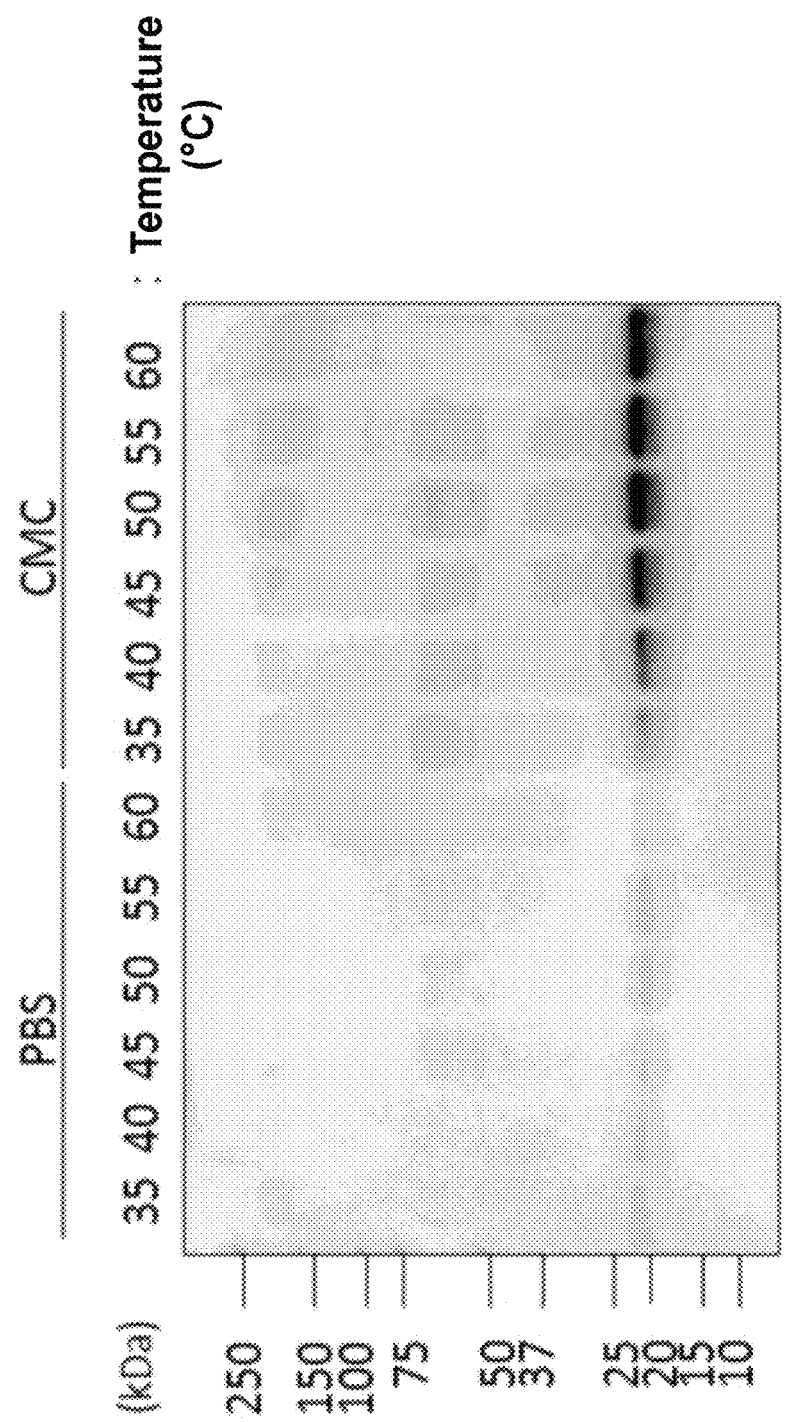
FIG. 9A is a diagram depicting results of a western blotting with a biotinylated anti-CD9 antibody of samples that are obtained by immunoprecipitating a serum specimen diluted with PBS or CMC-PBS together with an anti-CD9 antibody at different temperatures ranging from 35 to 60° C., in Example 9.
Figure 9B:
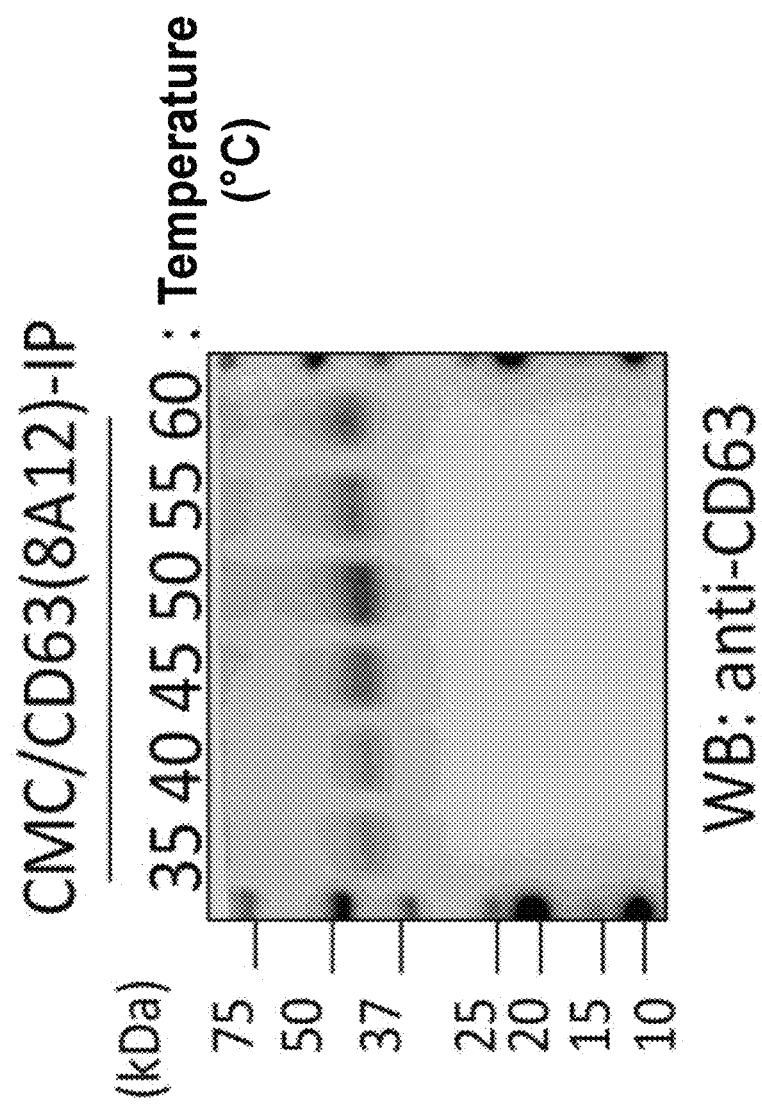
FIG. 9B is a diagram depicting results of a western blotting with an anti-CD63 antibody of samples that are obtained by immunoprecipitating a serum specimen diluted with CMC-PBS together with an anti-CD63 antibody at different temperatures ranging from 35 to 60° C., in Example 9.
Figure 9C:
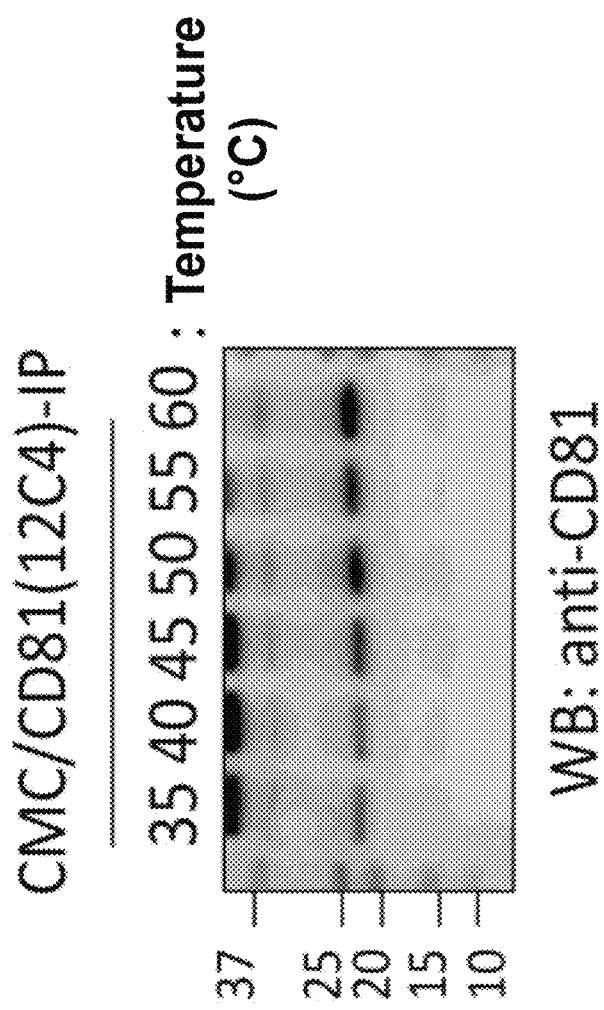
FIG. 9C is a diagram depicting results of a western blotting with an anti-CD81 antibody of samples that are obtained by immunoprecipitating a serum specimen diluted with CMC-PBS together with an anti-CD81 antibody at different temperatures ranging from 35 to 60° C., in Example 9.

The healthy human serum was centrifuged at 20,000×g at 4° C. for 15 minutes, then 100 μL of the serum was diluted with 100 μL of PBS, or CMC-PBS (final concentration of 0.5 wt % after the dilution of the serum). Then, the magnetic beads (Dynabeads M-280 tosylactivated (Life Technologies)) to which the anti-CD9 antibody (our product), the anti-CD63 antibody (8A12: Cosmo Bio Co., Ltd.) or the anti-CD81 antibody (12C4: Cosmo Bio Co., Ltd.) is attached, are added to the resultant solution to achieve 0.26 mg/mL. After the reaction at each temperature for 5 minutes, the magnetic beads were washed three times with PBS-T, then diluted with the sample buffer (Bio-Rad Laboratories, Inc.) for preparation of the western blotting sample. The EV recovery efficiency was analyzed by western blotting method with use of the biotinylated anti-CD9 antibody (our product), anti-CD63 antibody (our product), and anti-CD81 antibody (12C4: Cosmo Bio Co., Ltd.) (FIG. 9A to FIG. 9C). Improvement of EV recovery efficiency was recognized under each temperature ranging from 35° C. to 60° C. with the addition of CMC. Further improvement of EV recovery efficiency was recognized under high temperatures more than 40° C. with the addition of CMC. The improvement of EV recovery efficiency using CMC can be recognized also for short-time reactions.

Example 10

Viscosity in the PBS solution was measured for the cellulose derivatives used in Example 7 and polyvinylpyrrolidone used in Example 8. Specifically, the viscosity was obtained as an average of results that were measured at 30° C. for 60 seconds under different rotation speeds at 200 rpm, 400 rpm, 600 rpm and 800 rpm with use of a viscosity analyzer, Rheology Spectrometer SKR100 (Yamato Scientific Co., Ltd.), for each of PBS solutions that are prepared by dissolving each of the cellulose derivatives or polyvinylpyrrolidone in PBS to achieve 2 wt % (Table 4).

TABLE 4

Viscosities of cellulose derivatives and polyvinylpyrrolidone used in Example.

| | Product name | Viscosity/Measurement condition |
|---|---|---|
| Hydroxyethyl cellulose (HEC) CAS No. 9004-62-0 | HEC 380 kDa #308633 | 207.8 mPa · s/ 2 wt % PBS solution (30° C.) |
| Hydroxypropyl methylcellulose (HPMC) CAS No. 9004-65-3 | HEMC 80-120 cP #H9262 | 48.6 mPa · s/ 2 wt % PBS solution (30° C.) |
| Polyvinylpyrrolidone (PVP) CAS No. 9003-39-8 | PVP K-30 28314-82 nacalai | 1.5 mPa · s/ 2 wt % PBS solution (30° C.) |
| | PVP K-90 28315-72 nacalai | 5.8 mPa · s/ 2 wt % PBS solution (30° C.) |

Example 11

The influences on the EV recovery by means of immunoprecipitation using CMC (Sigma-Aldrich Co. LLC #C4888) and antibodies against tetraspanin membrane protein (CD9 and CD63) and detection of marker (EML4-ALK fusion gene) RNA from the EV, were investigated.

A culture supernatant of human lung carcinoma cell line H2228 cultured in serum-free medium for three days was used as a sample. The culture supernatant was centrifuged at 2,000×g at 4° C. for 5 minutes, then filtered through a 0.22 µm filter (manufactured by Millipore Corp.), and then concentrated using Amicon Ultra-15 (manufactured by Millipore Corp.) to 100-fold.

Figure 10:
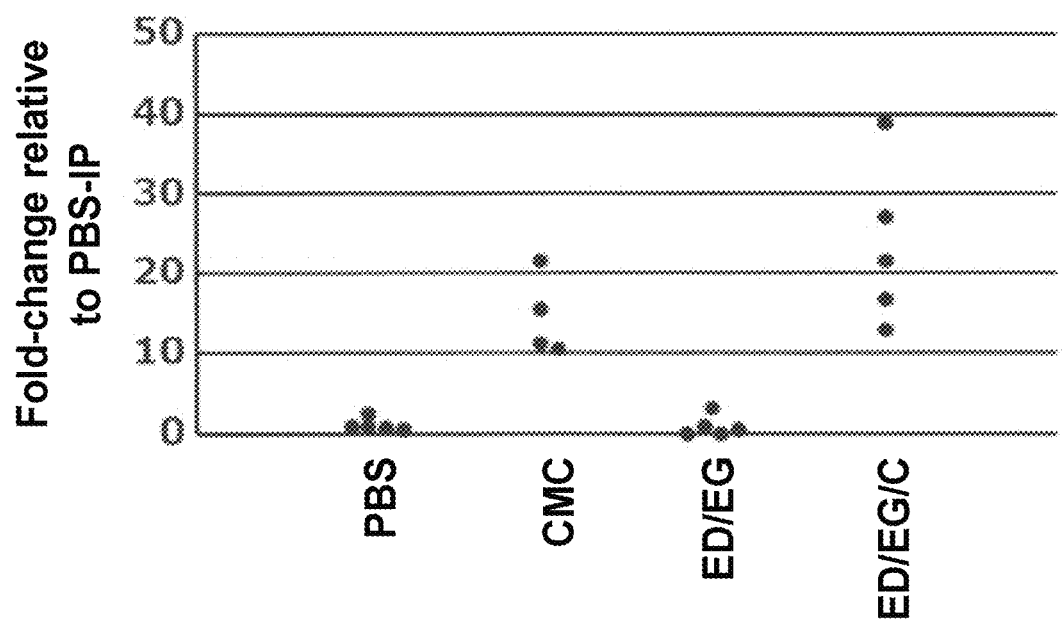
FIG. 10 is a plot diagram representing a detection amount (represented as a magnification change with reference to a sample diluted with PBS) of EML4-ALK mRNA of a sample that is diluted with PBS, CMC-PBS ("CMC") EDTA/EGTA-PBS ("ED/EG") or EDTA/EGTA/CMC-PBS ("ED/EG/C") and obtained by immunoprecipitation method using the anti-CD9 antibody or the anti-CD63 antibody of a culture supernatant of human lung carcinoma cell line H2228, in Example 11.

The concentrate was diluted with an equivalent amount of PBS, EDTA/EGTA-PBS (final concentration of 50 mM after the dilution of the concentrate, respectively) (ED/EG), CMC-PBS (final concentration of 0.5 wt % after the dilution of the concentrate) (CMC), or EDTA/EGTA/CMC-PBS (with final concentrations of 37.5 mM/37.5 mM/0.5 wt % after the dilution of the concentrate, respectively) (ED/EG/C). Then, Dynabeads M-280 tosylactivated (Life Technologies) to which the anti-CD9 antibody (our product) or the anti-CD63 antibody (our product) is attached, are added to the resultant solution to achieve 0.26 mg/mL. After the resultant solution underwent reaction while rotated at 4° C. overnight, the magnetic beads were washed three times with PBS-T, then total RNA was purified using miRNeasy micro kit (manufactured by QIAGEN). cDNA was prepared from the purified total RNA using Superscript (trademark) IV First-Strand Synthesis System (manufactured by Thermo Fisher Scientific), and then EML4-ALK mRNA was quantified by using Droplet Digital PCR (Bio-Rad Laboratories, Inc.) (FIG. 10).

For the detection of EML4-ALK mRNA, primers and a fluorescence probe with sequences in Table 5 shown below were used. As the fluorescence probe, a double quencher probe having a fluorescent substance HEX at 5'-terminal and ZEN quencher in the probe and Iowa Black (registered trademark) quencher (IABkFQ) at 3'-terminal, was used. With use of the primers and fluorescence probes listed in Table 5, it is possible to detect variants 3a and 3b of the EML4-ALK fusion gene.

TABLE 5

Probe and primers for detection of EML4-ALK mRNA

| Primer/probe | sequence |
|---|---|
| Forward primer | CAGATGATAGCCGTAATAAATTGTCG (SEQ ID No: 1) |
| Reverse primer | CTTCCGGCGGTACACTTGG (SEQ ID No: 2) |
| Fluorescence probe | /5HEX/ACTGCAGAC/ZEN/AAGCATAAAGATGTCA (SEQ ID No: 3)/3IABkFQ |

EML4-ALK contained in the EV that was recovered by immunoprecipitation method, was detected. With use of CMC, it is possible to increase the detection amount of EML4-ALK mRNA, demonstrating that the EV recovery efficiency was improved. With the addition of the chelating agent, it is possible to further increase the detection amount of EML4-ALK mRNA, demonstrating that the EV recovery efficiency was further improved.

SEQUENCE LISTING

The invention claimed is:

1. A method of recovering an extracellular vesicle, the method comprising:
   separating the extracellular vesicle from an extracellular vesicle-containing sample in the presence of a polymer,
   wherein the separation is performed by an extracellular vesicle membrane-binding material comprising an antibody against an extracellular vesicle marker or an antigen-binding fragment thereof,
   wherein the polymer comprises carboxymethyl cellulose, hydroxyethyl cellulose, hydroxypropyl cellulose, or hydroxypropylmethyl cellulose,
   wherein the antibody is against CD9, CD63, CD81, or CD147.

2. The method of claim 1, wherein an aqueous solution of the polymer, at a concentration in a range of from 1 to 20 wt. %, at a temperature in a range of from 20 to 30° C., has a viscosity of 1.5 mPa's or more in.

3. The method of claim 1, wherein the polymer has a weight average molecular weight of 10 kDa or more.

4. The method of claim 1, wherein a concentration of the polymer used in the separation of the extracellular vesicle from the extracellular vesicle-containing sample is in a range of from 0.01 to 10.00 wt %.

5. The method of claim 1, further comprising:
   mixing the extracellular vesicle-containing sample with a chelating agent.

6. The method of claim 1, wherein the extracellular vesicle is an exosome.

7. The method of claim 1, wherein the extracellular vesicle-containing sample is a blood sample, urine, or saliva.

8. A method of analyzing an extracellular vesicle, the method comprising:
   separating the extracellular vesicle from an extracellular vesicle-containing sample in the presence of a polymer, to obtain a separated extracellular vesicle; and
   analyzing the separated extracellular vesicle,
   wherein the separation is performed by an extracellular vesicle membrane-binding material comprising an antibody against an extracellular vesicle marker or an antigen-binding fragment thereof,
   wherein the polymer comprises carboxymethyl cellulose, hydroxyethyl cellulose, hydroxypropyl cellulose, or hydroxypropylmethyl cellulose
   wherein the antibody is against CD9, CD63, CD81, or CD147.

9. The method of claim 8, further comprising adding a chelating agent to the extracellular vesicle-containing sample.

10. The method of claim 8, further comprising analyzing a protein or a nucleic acid in the separated extracellular vesicle.

11. A kit, comprising:
a polymer; and
an extracellular vesicle membrane-binding material,
wherein the extracellular vesicle membrane-binding material comprises an antibody against an extracellular vesicle marker or an antigen-binding fragment thereof,
wherein the polymer comprises carboxymethyl cellulose, hydroxyethyl cellulose, hydroxypropyl cellulose, or hydroxypropylmethyl cellulose,
wherein the antibody is against CD9, CD63, CD81, or CD147.

12. The kit of claim 11, further comprising:
a chelating agent.

13. The method of claim 1, wherein the polymer has a weight average molecular weight of 90 kDa or more.

14. The method of claim 1, wherein the polymer has a weight average molecular weight of 5000 kDa or less.

15. The method of claim 1, wherein a concentration of the polymer used in the separation of the extracellular vesicle from the extracellular vesicle-containing sample is in a range of from 0.10 to 5.00 wt %.

16. The method of claim 1, wherein the separation is performed by the extracellular vesicle membrane-binding material without precipitating the extracellular vesicle with the polymer.

17. The method of claim 5, wherein the chelating agent has 2 or more coordination moieties.

18. The method of claim 5, wherein the chelating agent includes one selected from the group consisting of oxalic acid, hydroxyethyl iminodiacetic acid (HIDA), nitrilotriacetic acid (NTA), hydroxyethyl ethylenediaminetriacetic acid (HEDTA), ethylenediaminetetraacetic acid (EDTA), ethylenediaminetetra(methylene phosphonic acid) (EDTMP), glycoletherdiaminetetraacetic acid (EGTA), and salts thereof.

19. The method of claim 5, wherein the chelating agent is present at a concentration of 1 mM to 200 mM during the separation.

* * * * *